US008841094B2

(12) United States Patent
Kurosawa et al.

(10) Patent No.: US 8,841,094 B2
(45) Date of Patent: Sep. 23, 2014

(54) HOMOLOGOUS RECOMBINATION METHOD, CLONING METHOD, AND KIT

(75) Inventors: Nobuyuki Kurosawa, Toyama (JP); Masaharu Isobe, Toyama (JP)

(73) Assignee: National University Corporation University of Toyama, Toyama-shi (JP)

( * ) Notice: Subject to any disclaimer, the term of this patent is extended or adjusted under 35 U.S.C. 154(b) by 625 days.

(21) Appl. No.: 12/921,367

(22) PCT Filed: Mar. 6, 2009

(86) PCT No.: PCT/JP2009/054325
§ 371 (c)(1),
(2), (4) Date: Dec. 8, 2010

(87) PCT Pub. No.: WO2009/110606
PCT Pub. Date: Sep. 11, 2009

(65) Prior Publication Data
US 2011/0117609 A1    May 19, 2011

(30) Foreign Application Priority Data
Mar. 7, 2008   (JP) ................................ 2008-057995

(51) Int. Cl.
| C12Q 1/68 | (2006.01) |
| C12N 15/00 | (2006.01) |
| C12N 15/64 | (2006.01) |
| C12N 15/66 | (2006.01) |
| C12N 15/10 | (2006.01) |

(52) U.S. Cl.
CPC ............ C12N 15/66 (2013.01); C12N 15/1082 (2013.01)
USPC ...... 435/91.2; 435/6.1; 435/320.1; 435/91.41

(58) Field of Classification Search
None
See application file for complete search history.

(56) References Cited

U.S. PATENT DOCUMENTS

| 5,518,901 A * | 5/1996 | Murtagh ...................... 435/91.2 |
| 2003/0199037 A1* | 10/2003 | Harris et al. .................. 435/69.1 |
| 2007/0148775 A1 | 6/2007 | Lee et al. |

FOREIGN PATENT DOCUMENTS

| WO | WO 99/29837 A2 | 6/1999 |
| WO | WO 01/04288 A1 | 1/2001 |
| WO | WO 0104288 A1 * | 1/2001 |
| WO | WO 02083871 A2 * | 10/2002 |
| WO | WO 2007/014275 A2 | 2/2007 |

OTHER PUBLICATIONS

Chartier et al. (J Virol. 1996 Jul;70(7):4805-10, p. 4806).*
Chartier et al. (Efficient generation of recombinant adenovirus vectors by homologous recombination in *Escherichia coli*, J. Virol., Jul. 1996, vol. 70, No. 7, pp. 4805-4810).*
Oliner et al. (In vivo cloning of PCR products in *E. coli*, Nucleic Acids Res., Nov. 11, 1993, vol. 21, No. 22, pp. 5192-5197), Stewart (WO 2001/1004288, published Jan. 18, 2001).*
Berrow et al. (A versatile ligation-independent cloning method suitable for high-throughput expression screening applications, Nucleic Acids Res., Mar. 2007, Vol.35, No. 6, e45).*
Forms PCT/ISA/237, PCT/ISA/326, PCT/IS/338,and PCT/IB/373, (eleven (11) pages), Sep. 16, 2000.
Zhang et al., A new logic for DNA engineering using recombination in *Escherichia coli*, Nature Genetics, Oct. 1998, pp. 123-128, vol. 20.
Zhang et al., DNA cloning by homologous recombination in *Escherichia coli*, Nature Biotechnology, Dec. 2000, pp. 1314-1317, vol. 18.
Hamilton et al., Duplex strand joining reactions catalyzed by vaccinia virus DNA polymerase, Nucleic Acids Research, 2007, pp. 143-151, vol. 35.
Japanese Office Action of JP Application No. 2010-501983 with English translation, Oct. 23, 2012.
Oliner et al., In vivo cloning of PCR products in *E. coli*, Nucleic Acids Rec., Nov. 11, 1993, vol. 21, No. 22, pp. 5192-5197.
Berrow et al., A versatile ligation-independent cloning method suitable for high-throughput expression screening applications, Nucleic Acids Res., Mar. 2007, vol. 35, No. 6, e45.
Chartier et al., Efficient generation of recombinant adenovirus vectors by homologous recombination in *Escherichia coli*, J. Virol., Jul. 1996, vol. 70, No. 7, pp. 4805-4810.
International Search Report of PCT/JP2009/054325, Sep. 11, 2009.
Adolfo Rivero-Müller et al., "Assisted Large Fragment Insertion by Red/ET-recombination (ALFIRE)—An Alternative and Enhanced Method for Large Fragment Recombineering", Nucleic Acids Research, 2007, vol. 35, No. 10, (Eight (8) pages).
Laurent Mallet et al., "Intergenic Flip Flop, A Method for Systematic Gene Disruption and Cloning in Yeast", Yeast Fundamental Analysis Reports, 1996, pp. 1361-1357, vol. 12, XP008069255.
Gerald Marsischky et al., "Many Paths to Many Clones: A Comparative Look at High-Throughput Cloning Methods", Genome Research, 2004, pp. 2020-2028, vol. 14.
Quinn Lu, "Seamless Cloning and Gene Fusion", Trends in Biotechnology, Apr. 2005, pp. 199-207, vol. 23, No. 4.
Arne Skerra, "Phosphorothioate Primers Improve the Amplification of DNA Sequences by DNA Polymerases with Proofreading Activity", Nucleic Acids Research, 1992, pp. 3551-3554, vol. 20, No. 14, XP000651211.
European Search Report dated Sep. 2, 2011 (Eight (8) pages).
Japanese Office Action with English Translation dated Mar. 5, 2013 (four (4) pages).
European Office Action dated May 22, 2013 (six (6) pages).
Australian Office Action dated Jul. 8, 2013 (Three (3) pages).
European Office Action dated Feb. 28, 2014 (Five (5) pages).
Japanese Office Action dated Apr. 30, 2014 with English translation (Nine (9) pages).

* cited by examiner

*Primary Examiner* — Christopher M Babic
*Assistant Examiner* — Aaron Priest
(74) *Attorney, Agent, or Firm* — Crowell & Moring LLP

(57) ABSTRACT

The present invention provides a method which can achieve the homologous recombination of a gene of interest selectively, and a recombinant DNA molecule produced by the method. A homologous recombination method which uses a PCR product and a linearized vector is disclosed. The PCR product comprises a sequence for a target gene and amplification primer sequences P1 and P2 on both terminal ends. The vector contains homologous recombination regions VP1 and VP2 which respectively comprise nucleotide sequences homologous to P1 and P2, and at least one a homologous recombination region VT (VT1 and/or VT2), which comprises a nucleotide sequence homologous to a sequence T (T1 and/or T2), T sequences are sequence parts internal to P1 and/or P2 as well as sequence parts on the terminal side of VP1 and/or VP2 (provided that at least one T sequence has a nucleotide sequence specific to the target gene).

13 Claims, 16 Drawing Sheets

Fig. 4
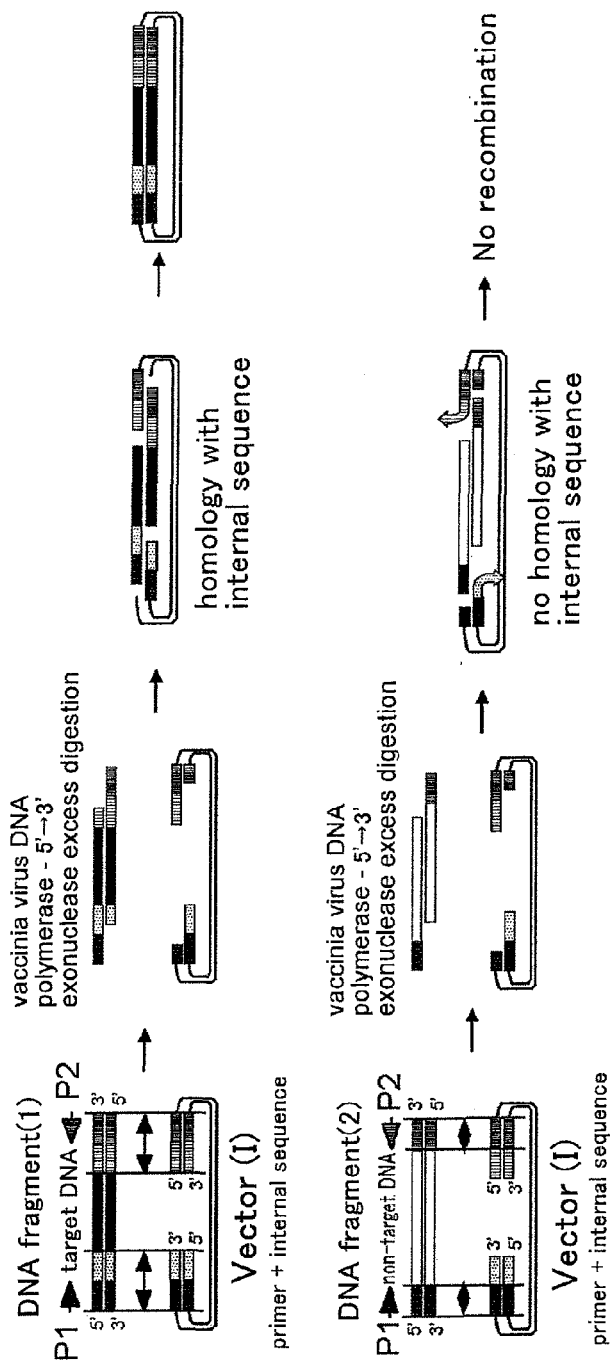
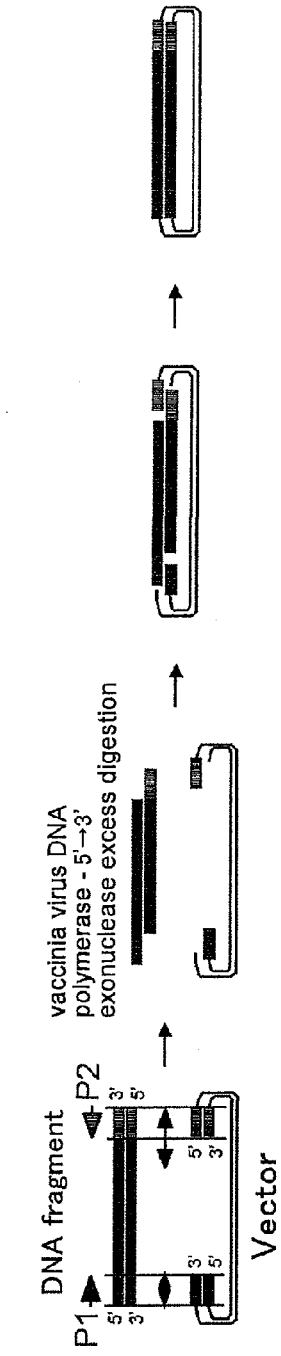

Fig. 8

DNA fragment 1 nucleotide sequence
(shaded portion: homologous recombination region, □: internal sequence, →: primer sequence)

primer (a)

CTTCGAATTCTGCAGTCGACGGTACCGCGGGCCCGGGATCCCCCCCCCGA|CATAACAACCAGAATCCTCCTCTAAAG
AAGCACCTGGGAGCACAGCTCATCACCATGGACTGGACCTGGAGGTTCCTCTTTGTGGCAGCAGTACAGGTGTCCA
GTCCCAGGTCCAGCTGGTGCAATCTGGGGCTGAGGTGAAGAAGCCTGGGTCCTCGGTGAAGATCTCCTGCAAGGCTTCTG
GAGGCACCTTCAGCAGCTATACTTTCACCTGGGTGCGACAGGCCCCTGGACAAGGGCTTGAGTGGATGGGAAGGATCATC
CCCAATGTCGGTATAGCAAACTACGCACAGAAGTTCCAGGGCAGAGTCACGCTTATCGCGGACACAAATTCACGAATTCAAC
GTACATGGAGCTGAGCAGCTGAGATCTGATGACACGGCCGTTTATTTTTGTGCCGAGACCCCTCGGGCCACTCACATG
ACTACTGGGGCCAAGGAACCCTGGTCACCGTCTCCTCAGCTTCACCAAGGGCCCATCCGTCTTCCCCCTGGCCCCTGC
TCCAGGAGCACCTCCGAGAGCACCTGACGCAGGGGTGCACACCTTCCCGGCT primer (b)

Fig. 9

DNA fragment 2 nucleotide sequence
(shaded portion: homologous recombination region, →: primer sequence)

primer (a)
CTTCGAATTCTGCAGTCGACGGTACCGGGGGGCCCGGATCCACCGGTCGCCACCATGGTGAGCAAGGGCGAGGAGCTGTT
CACCGGGGTGGTGCCCATCCTGGTCGAGCTGGACGGCGACGTAAACGGCCACAAGTTCAGCGTGTCCGGCGAGGGCGAGG
GCGATGCCACCTACGGCAAGCTGACCCTGAAGTTCATCTGCACCACCGGCAAGCTGCCCGTGCCCTGGCCCACCCTCGTG
ACCACCCTGACCTACGGCGTGCAGTGCTTCAGCCGCTACCCCGACCACATGAAGCAGCACGACTTCTTCAAGTCCGCCAT
GCCCGAAGGCTACGTCCAGGAGCGCACCATCTTCTTCAAGGACGACGGCAACTACAAGACCCGCGCCGAGGTGAAGTTCG
AGGGCGACACCCTGGTGAACCGCATCGAGCTGAAGGGCATCGACTTCAAGGAGGACGGCAACATCCTGGGGCACAAGCTG
GAGTACAACTACAACAGCCACAACGTGTATATCATGGCCGACAAGCAGAAGAACGGCATCAAGGTGAACTTCAAGATCCG
CCACAACATCGAGGACGGCAGCGTGCAGCTCGCCGACCACTACCAGCAGAACACCCCCATCGGCGACGGCCCCGTGCTGC
                                        ←
                                        primer (b)

Fig. 10

Vector I sequence (shaded portion: homologous recombination region,
☐: internal sequence, underline: restriction enzyme digestion sequence)

HindIII   primer (a)                                                                    EcoRV
AAGCTTCGAATTCTGCAGTCGACGGTACCGCGGGCCCGGGGATCCCCCCCCCCCCGGGAGATATC————SacB EcoRV
                                                                                        GATATC
CGTGGAACTCAGGCGCCCTGACCAGCGGGGTGCACACGTTCCCGGCTGTCCTACAGTCCTCAGGACTCTACTCCCTCAGC
                                    ←——————— primer (b)
negative selection marker gene (2.Kb)

AGCGTGGTGACCGTGCCCTCCAGCAGCTTGGGCACCCAGACCTACACCTGCAACGTGAATCACAAGCCCAGCAACACCAA
GGTGGACAAGAGAGTTGAGCCCAAATCTTGTGACAAAACTCACACAGCTGCCCAGCACATGCCCAGCACCTGAACTCCTGGGGG
GACCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAATGCCAAGACAAA
GCCGCGGGAGGAGCAGTACAACAGCACGTACCGTGTGTCAGCGTCCTCACCGTCCTGCACCAGGACTGGCTGAATGGCA
AGGAGTACAAGTGCAAGGTCTCCAACAAAGCCCTCCCAGCCCCCATCGAGAAAACCATCTCCAAAGCCAAAGGGCAGCCC
CGAGAACCACAGGTGTACACCCTGCCCCCATCCCGGGATGAGCTGACCAAGAACCAGGTCAGCCTGACCTGCCTGGTCAA
AGGCTTCTATCCCAGCGACATCGCCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAGCAGGTGGCAGCAGGGGAACGTCTTC
TCATGCTCCGTGATGCATGAGGGTCTGCACAACCACTACACGCAGAAGAGCCTCTCCCTGTCTCCGGGTAAATGAgtgcg acggcggccgc
NotI

Fig. 11

Vector II sequence (shaded portion: homologous recombination region, underline: restriction enzyme digestion sequence)

HindIII     primer (a)                                    EcoRV
AAGCTTCGAATTCTGCAGTCGACGGTACCGCGGGCCCGGGATCCGATATC————————————SacB EcoRV
negative selection marker gene—(2.Kb)————————————GATATC
CAGCGGGCGTGCACACCTTCCCGGCTGTCCTACAGTCCTCAGGACTCCTACTCCCTCAGCAGCGTGGTGACCGTGCCCTCCA
          primer (b)
GCAGCTTGGGCACCCAGACCTACAGCCTGAATCACAGAGCCCAGCAACACCAAGGTGGACAAGAGAGTTGAGCCC
AAATCTTGTGACAAAACTCACACATGCCCACCGTGCCCAGCACCTGAACTCCTGGGGGACCGTCAGTCTTCCTCTTCCC
CCCAAAACCCAAGGACACCCTCATGATCTCCCGGACCCCTGAGGTCACATGCGTGGTGGTGGACGTGAGCCACGAAGACC
CTGAGGTCAAGTTCAACTGGTACGTGGACGGCGTGGAGGTGCATAATGCCAAGACAAAGCCGCGGGAGGAGCAGTACAAC
AGCACGTACCGTGTGGTCAGCGTCCTCACCGTCCTGCACCAGGACTGGCTGAATGGCAAGGAGTACAAGTGCAAGGTCTC
CAACAAAGCCCTCCCAGCCCCCATCGAGAAAACCATCTCCAAAGCCAAAGGGCAGCCCCGAGAACCACAGGTGTACACCC
TGCCCCCATCCCGGGATGAGCTGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTGGACTCCGACGGCTCCTT
CTTCCTCTACAGCAAGCTCACCGTGGACAAGAGCAGGTGGCAGCAGGGGAACGTCTTCTCATGCTCCGTGATGCATGAGG
GTCTGCACAACCACTACACGCAGAAGAGCCTCTCCCTGTCTCCGGGTAAATGAgtgcgacgcggccggc NotI IgG, GFP: control DNA
*: GFP derived DNA fragment 2

IgG, GFP: control DNA
*: GFP derived DNA fragment 2

IgG, GFP: control DNA
*: GFP derived DNA fragment 2

Lane 1: PCR reaction without a template
Lane 2: PCR reaction with template cDNA
*: non-target PCR product ← 1.5kb ← 1.5kb immunoglobulin Fig. 20
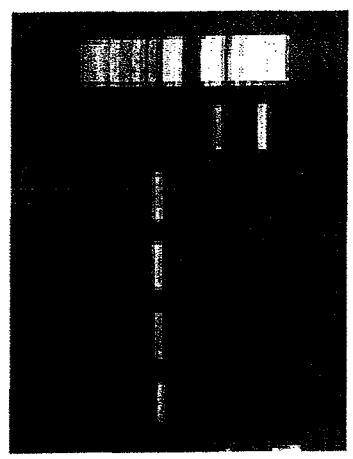
vector 1
DNA fragment 1-(e)
DNA fragment 1-(d)
DNA fragment 1-(c)
DNA fragment 1-(b)
Fig. 21
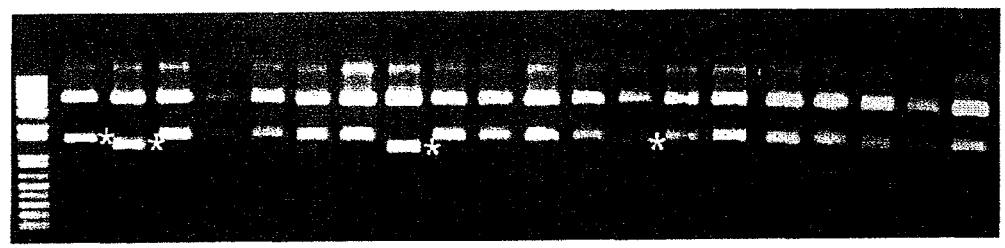
*: non-specific DNA fragment

HOMOLOGOUS RECOMBINATION METHOD, CLONING METHOD, AND KIT

CROSS-REFERENCE TO RELATED APPLICATION(S)

This application is a national stage of PCT International Application No. PCT/JP 2009/054325, filed on Mar. 6, 2009 which claims the priority of Japanese application of 2008-57995, filed on Mar. 7, 2008, and the entirety of which is hereby incorporated herein by reference.

TECHNICAL BACKGROUND

The present application relates to a homologous recombination method for a gene and a cloning method for a target gene, as well as a kit which is used for those methods.

BACKGROUND ART

DNA cloning refers to a technique for producing a large amount of the same gene family by connecting a gene of interest to a self-replicable vector, such as plasmid, phage or cosmid, and introducing the vector into a host such as E. coli to proliferate the gene. Cloning and sub-cloning in E. coli is performed by a method containing connecting a gene of interest, which is amplified by a method such as polymerase chain reaction (PCR), to a vector having a replication origin and an antibiotic selection marker by using DNA ligase, introducing the resulting vector into E. coli cells, and selecting cells with measuring antibiotic resistance of the cells.

Such general cloning technique is the basis of modern bioengineering, and is widely used for the cloning and high speed protein expression of mass amount of genes based on genetic information which has significant developed after the completion of the human genome project. However, in operations of genes under the prior method there are some limitations in that an inserted DNA and a vector should be digested by a restriction enzyme at the same recognition site and that a restriction enzyme should be selected from those which does not digest the inside of the inserted DNA or vector. Also, a high level skill is required in the process of treating a restriction enzyme and a ligase, and further a high cost is not disregarded because of the use of expensive enzymes.

In or after 1990s, interest in a genetic engineering technique, which uses a sequence specific gene recombination enzyme that recognizes a specific nucleotide sequence to induce the recombination between DNA fragments, has increased. Particularly, a Gateway system (Invitrogen, Co.) for cloning genes by using a gene integrase, which recognizes specific DNA sequences such as attL, attR, attB and attP, has been developed and widely used in rapid cloning and protein expression of mass amount of genes. This method is carried out by in vitro gene manipulation in the same manner as the conventional restriction enzyme-ligation reaction, but it is a novel cloning method which utilizes LR clonase mediating a linear DNA fragment having attL or attR, and BP clonase recognizing between attP and attB. In this method, first, a gene of interest can be cloned into an insertion vector by conventional gene manipulations, and by utilizing specific recombination sequences such as attL, attR, attB and attP existing in the insertion vector and a clonase recognizing those sequences a homologous recombination reaction is conducted, thereby transfer of a gene into various expression vectors having the same specific recombination sequence becomes feasible. This method is effective for rapid sub-cloning and verification of expression of mass amount of genes, but first, it requires that DNA fragment of interest should be cloned into insertion vector by a conventional cloning method and is not suitable for cloning of any DNA fragment which does not have any specific recombination sequence.

On the other hand, in E. coli cells, proteins RecA and RecBCD, which engage in repair for double-strand break, catalyze homologous recombination reaction. In this recombination reaction, homologous recombination may be occurred if DNA fragments showing sequences identical at several hundred or more nucleotides exist. However, if the homologous DNA length is equal to or less than 40 to 50 nucleotides, genetic recombination by E. coli itself is quite difficult to occur and recombination between homologous genes is able to be occurred only when phage-derived recombination enzyme Red(Red α/β) or RecE/T system is introduced. This genetic recombination utilizing DNA fragment having a short homologous region can be used, for example, in a technique for manipulating a gene of microorganism, or an intracellular cloning which is not affected by restriction enzymes or ligases. Referring Non-patent Publication 1 and Patent Document 1.

Non-patent Publication 1: Zhang et al., 1998, Nature Genetics, 20, 123-128, Zhang et al., 2000, Nature Biotechnology 18, 1314-1317.

Patent Document 1: Japanese Laid Open Patent Publication Tokuhyou 2002-503448 (corresponding to WO 99/29837).

The entireties of the Non-patent Publication 1 or Patent Document 1 are hereby incorporated herein by reference.

SUMMARY OF INVENTION

Technical Problem

If an intracellular cloning is conducted by using homologous recombination reaction between a linearlized plasmid vector and a PCR product, first, sequence homologous regions having its length of 50 nucleotides are positioned on both ends of an inserted DNA, and a vector is digested by a restriction enzyme so that sequence homologous regions are positioned on both ends, then those are introduced into E. coli having homologous recombination enzyme (recombinase).

The inserted DNA is prepared for example as a PCR product, but there might be the case that a region sandwiched by the sequence homologous regions of both ends is not a target region as the subject for cloning because of non-specific amplification reaction when during PCR process the binding specificity of a primer to a template is low, a template has several number of sequences similar to the primer sequence, and others.

Even when the region sandwiched by the sequence homologous regions is not a target region as the subject for cloning, the region is cloned by the sequence homologous regions existing in the primer in the same manner as a gene of interest.

The object of the present invention is to provide a homologous recombination method used for cloning genes by using homologous recombination, which method can achieve selective homologous recombination of a gene of interest.

The further object of the present invention is to provide a cloning method for a target gene, which method includes amplification of recombinant DNA molecule obtained by using the above mentioned homologous recombination method capable of achieving selective homologous recombination of a gene of interest.

Solution to Problem

In a general homologous recombination, homologous recombination regions existing on both ends of a linearlized vector are the same as homologous regions existing on an amplification primer sequence. In contrast, according to the present invention a homologous recombination regions of a linearlized vector is characterized by that, in addition to a sequence of an amplification primer, an internal sequence of the amplification primer sequence which only exists in a target gene is added to the vector and thereby out of amplified products obtained by the use of the amplification primer a target DNA is selectively subject to homologous recombination.

The present invention is indicated below.

[1] A method for homologous recombination comprising:
using a PCR product and a linearlized vector, in which the PCR product contains a target gene sequence having amplification primer sequences P1 and P2 on its both ends, and the linearlized vector has homologous recombination regions VP1 and VP2 comprising nucleotide sequences homologous to the amplification primer sequences P1 and P2 of the PCR product and the linearlized vector also has a homologous recombination region VT1 comprising a nucleotide sequence homologous to a sequence T1 which is a part of sequence in the PCR product internal to P1 on the terminal side of VP1 and/or a homologous recombination region VT2 comprising a nucleotide sequence homologous to a sequence T2 which is a part of sequence in the PCR product internal to P2 on the terminal side of VP2, provided that at least one of T1 and T2 has a nucleotide sequence specific to the target gene;
making the PCR product be subject to homologous recombination reaction and thereby be inserted into the vector; and
obtaining a recombinant DNA molecule in which a PCR product of interest is specifically inserted into a vector.

[2] The method described in [1], in which both T1 and T2 have a nucleotide sequence specific to the target gene.

[3] The method described in [1] or [2], in which at least one of the amplification primers P1 and P2 has a nucleotide sequence specific to the target gene.

[4] The method described in any one of [1] to [3], in which the PCR product is prepared by two times of PCR operations, the first PCR operation is conducted by using an amplification primer containing T1 sequence and an amplification primer containing P3 sequence, provided that the P3 sequence has no homology to any of homologous recombination regions of the vector VT1, VP1, VT2 and VP2, and the second PCR operation is conducted by using an amplification primer containing P1 sequence and an amplification primer containing P2 sequence.

[5] The method described in [4], in which the 3'-terminal side region of the amplification primer containing P1 sequence and the 5'-terminal side region of the amplification primer containing T1 sequence have a partially overlapped sequence, and the amplification primer containing P2 sequence and the amplification primer containing P3 sequence have or do not have a partially overlapped sequence.

[6] The method described in any one of [1] to [5], in which the amplification primer sequences P1 and P2 have 10 or more bases independently.

[7] The method described in any one of [1] to [6], in which the homologous recombination regions of the vector VP1+VT1 and VP2+VT2 have 11 or more bases independently.

[8] The method described in any one of [1] to [7], in which one or both of the amplification primers corresponding to sequences P1 and P2 are derived from nuclease resistant oligo primer.

[9] The method described in any one of [1] to [8], in which the target gene is an antibody gene or T-cell receptor gene and contains a sequence derived from constant region and variable region of the antibody gene or the T-cell receptor gene, and at least one of the homologous recombination regions of the vector VP1+VT1 and VP2+VT2 is derived from constant region of the antibody gene or the T-cell receptor gene.

[10] The method described in [9], in which another of the homologous recombination regions of the vector VP1+VT1 and VP2+VT2 has a sequence which is not derived from the antibody gene or the T-cell receptor gene.

[11] The method described in any one of [1] to [10], in which the homologous recombination reaction is conducted in a cell by using Red (Red α/β) or RecE/T system.

[12] The method described in any one of [1] to [10], in which the homologous recombination reaction is conducted by using In-Fusion® method.

[13] A cloning method for a target gene comprising:
preparing a recombinant DNA molecule in which a PCR product of interest is specifically inserted into a vector, and amplifying a recombinant having the recombinant DNA molecule.

[14] A kit containing a linearlized vector used for a homologous recombination method comprising the preparation of a recombinant DNA molecule in which a PCR product, which comprises a target gene sequence, having amplification primers P1 and P2 on both ends is specifically inserted into a vector, in which the linearlized vector has homologous recombination regions VP1 and VP2 comprising a nucleotide sequence homologous to the amplification primer sequences P1 and P2 of the PCR product and the linearlized vector also has a homologous recombination region VT1 comprising a nucleotide sequence homologous to a sequence T1 that is a part of sequence in the PCR product internal to P1 on the terminal side of VP1 and/or a homologous recombination region VT2 comprising a nucleotide sequence homologous to a sequence T2 that is a part of sequence in the PCR product internal to P2 on the terminal side of VP2 .

[15] The kit described in [14], in which the homologous recombination reaction is the method described in any one of [1] to [12].

[16] The kit described in [14] or [15], in which the recombinant DNA molecule is used for a cloning method for a target gene which method comprises amplification of a recombinant body having the recombinant DNA molecule.

Effect of Invention

According to the method of the present invention (the method utilizing internal sequence dependent homologous recombination reaction), even when a target DNA fragment and a non-target DNA fragment co-exist and are mixed, without purifying the target DNA fragment (without removing the non-target DNA fragment) the target DNA fragment can be inserted into a vector efficiently, and by using the vector in which the target DNA fragment is inserted cloning of the target DNA fragment can be conducted efficiently.

According to the method of the present invention (the method utilizing a PCR product amplified by using nuclease resistant oligo primer and internal sequence dependent homologous recombination reaction), even when a target DNA fragment and a non-target DNA fragment are co-exist and are mixed, without purifying the target DNA fragment (without removing the non-target DNA fragment) the target DNA fragment can be inserted into a vector with more provability (selectivity) as compared to that of the method utilizing the internal sequence dependent homologous recombination reaction mentioned above, and by using this vector in which the target DNA fragment is inserted cloning of the target DNA fragment can be conducted more efficiently.

Homologous Recombination Method

The homologous recombination method of the present invention comprises:

using a PCR product and a linearlized vector, in which the PCR product, which comprises a target gene sequence, having amplification primer sequences P1 and P2 on its both ends, and the linearlized vector has homologous recombination regions VP1 and VP2 comprising nucleotide sequences homologous to the amplification primer sequences P1 and P2 of the PCR product and the linearlized vector also has a homologous recombination region VT1 comprising a nucleotide sequence homologous to a sequence T1 that is a part of sequence in the PCR product internal to P1 on the terminal side of VP1 and/or a homologous recombination region VT2 comprising a nucleotide sequence homologous to a sequence T2 that is a part of sequence in the PCR product internal to P2 on the terminal side of VP2, provided that at least one of T1 and T2 has a nucleotide sequence specific to the target gene;

making the PCR product be subject to homologous recombination reaction and thereby be inserted into the vector; and obtaining a recombinant DNA molecule in which a PCR product of interest is specifically inserted into a vector.

General Homologous Recombination Method (FIG. 1)

In a general homologous recombination reaction (ET recombination reaction), as shown in the FIG. 1, by using a PCR product having amplification primer sequences P1 and P2 on its both ends (target DNA fragment (1) and non-target DNA fragment (2)) and a vector (II) having homologous recombination regions VP1 and VP2 which comprises a part or the entire of the amplification primer sequence and are positioned at or closed to the terminal side of the PCR product, the PCR product is inserted into the vector by homologous recombination.

In this case, recombination is occurred between the primer sequences P1 and P2 of the DNA fragment and the primer homologous sequences VP1 and VP2 of the linearlized vector. For this reason, when the target DNA fragment (1) and the non-target DNA fragment (2) co-exist and are mixed, unless there is a special condition such as lengths of the DNA fragments are significant different each other, both DNA fragments are inserted into the vector with the same probability. As shown in the FIG. 1, the target DNA fragment (1) and the non-target DNA fragment (2) are inserted into the vector (II) with the same probability.

Therefore, in a general homologous recombination method, when a target DNA fragment (1) and a non-target DNA fragment (2) co-exist and are mixed, the target DNA fragment (1) is purified (the non-target DNA fragment (2) is removed) in advance and then subject to homologous recombination reaction.

Internal Sequence Dependent Homologous Recombination Reaction (FIG. 2)

In contrast, in the present invention a homologous recombination region of a linearlized vector comprises two sequence elements, VP1 and VT1 (VP1+VT1) (and VP2 and VT2 (VP2+VT2)). The VP1 (and VP2) shares homology to P1 (and P2), and VT1 (and VT2) shares homology to T1 (and T2). The amplification primer P1 (and P2) positions on or closed to at least one terminal of PCR product, and T1 (and T2) is a part of sequence in the target DNA fragment (PCR product) internal to P1 (and P2). Also, a sequence T1 (and T2) internal to the amplification primer sequence positioned at one terminal side of the PCR product is a sequence derived from a template. As to a homologous recombination region of a vector, a part thereof is derived from the amplification primer sequence P1 (and P2) and a part of the remaining is derived from T1 (and T2) which is a part of the target gene sequence. Hereby, when a PCR product which has the amplification primer sequences on its both ends but has a sequence other than the target gene in the inside of the primer sequence, its amplification primer sequence portion is common but its target gene sequence portion is different, and thereby those sequences are not recognized as a homologous recombination region and homologous recombination is not occurred. Therefore, a PCR product having a sequence of a target gene of interest can be selectively inserted into a vector with homologous recombination. The method of the present invention can be called as internal sequence dependent homologous recombination reaction method.

As shown in the FIG. 2, the target DNA fragment (1) has on its both ends homologous recombination regions P1+T1 and P2+T2, a part of which is derived from an amplification primer sequence and a part of the remaining of which is derived from a part of a target gene sequence. In homologous recombination regions VP1+VT1 and VP2+VT2 of a linearlized vector (I), a part of which corresponds to a sequence derived from an amplification primer sequence and a part of the remaining of which corresponds to a sequence derived from a part of a target gene sequence. In this case (internal sequence dependent homologous recombination reaction utilizing ET recombination reaction), recombination based on a sequence derived from a complementary strand of the primer of the DNA fragment and recombination based on an internal sequence of the vector (a sequence derived from a part of the target gene sequence) are occurred. In the recombination reaction from the vector utilizing the internal sequence, only the specific recombination of the target DNA fragment (1) having the internal sequence in its homologous recombination region is occurred (route B), but the recombination of non-target DNA fragment (2) not having the internal sequence T1 and T2 in its homologous recombination region is not occurred (route D, here is no homology with the internal sequence). However, when recombination based on the complementary strand of the primer sequences P1 and P2 of the DNA fragment is occurred (routes A and C), both of the target DNA fragment (1) and the non-target DNA fragment (2) are inserted into a vector. As a result, when a target DNA fragment (1) and a non-target DNA fragment (2) co-exist and are mixed, the target DNA fragment (1) is subject to the routes A and B but the non-target DNA fragment (2) is subject only to the route C, and the former one is dominantly inserted into a vector.

In this regard, as long as at least one of the inside sequences (internal sequences) T1 and T2 of an amplification primer sequence positioned on the end of a PCR product is a sequence derived from a template, that is, template-specific (inherent) sequence, the effect of improving selectivity (specificity) of a target DNA fragment in homologous recombination is achieved, and the specificity of a PCR product having a target gene to be inserted into a vector in homologous recombination is significantly improved. The remaining internal sequence on another side may not be a template specific (inherent) sequence. However, if both T1 and T2 are template specific (inherent) sequences, the selectivity of a target DNA fragment in homologous recombination is high and more preferable.

Internal Sequence Dependent Homologous Recombination Reaction Utilizing S-oligo Primer (FIG. 3)

If a DNA fragment amplified by using a usual oligo DNA as a primer is introduced into E. coli with a linearlized vector and subject to ET recombination reaction, the DNA fragment is digested by 5'→3' exonuclease within a cell body. As a result, the DNA fragment with 3'-end overhanging structure is formed. The 3'-overhanging end is derived from a complementary strand of the primer sequence used in PCR. Similarly, the linearlized vector is digested by 5'→3' exonuclease and the vector with 3'-end overhanging structure is formed (referring the second drawings from the left in the FIG. 2). The 3'-overhanging end of the vector is derived from an internal sequence.

When recombination reaction between the 3'-overhanging end of the linearlized vector and the homologous region of the DNA fragment is conducted (routes B and C), because of utilizing internal sequence the target DNA only is inserted into the vector (route B in the FIG. 2). The non-target DNA fragment having an internal sequence is not subject to homologous recombination by this route, and is not inserted into a vector (route D in the FIG. 2). When the 3'-overhanging end of the DNA fragment and the homologous region of the vector are subject to recombination reaction (routes A and C), because of utilizing primer sequence, not only the target DNA fragment (route A in the FIG. 2) but also the non-target DNA fragment (route C in the FIG. 2) may be inserted into the vector, as described above.

Nucleotide molecules composing DNA are joined with phosphodiester bond via phosphoric acid, and an intracellular DNA degrading enzyme has an activity of cleaving phosphodiester bond. However, DNA having S-modified (phosphorothioated) phosphodiester or 2' 4'-BNA (Bridged Nucleic Acid) modified DNA are resistant to DNA degrading enzymes. In the present invention, the oligo primer resistant to these DNA degrading enzymes is called as nuclease resistant oligo primer. S-modified (phosphorothioated) oligo primer is a representative example of nuclease resistant oligo primer, but nuclease resistant oligo primer is not limited to S-oligo primer. S-modified DNA fragments amplified by PCR reaction with the use of S-modified oligo DNA (SP1, SP2) as a primer has S-modified sequence on its 5'-terminal side, and thereby, is particularly resistant to 5'→3' exonuclease digestion. For this reason, if the DNA fragment is introduced into E. coli with a vector and is subject to ET recombination reaction, it is not digested by 5'→3' exonuclease because S-modified DNA fragment has its S-modified 5'-terminal side (referring the second drawings from the left in the FIG. 3). As a result, 3'-overhanging end derived from a complementary sequence of a primer is not formed, and homologous recombination of S-modified DNA fragment addressed to the vector is not occurred (routes A and C, no recombination). In contrast, a linearlized vector is digested by 5'→3' exonuclease and 3'-end overhanging structure is formed. Since this 3'-overhanging end is derived from an internal sequence, only target S-modified DNA fragment homologous to this region becomes substrate for homologous recombination reaction (route B).

As described, since 5'-side of the DNA fragment is derived from S-modified oligo DNA, it is resistant to 5'→3' exonuclease digestion. Thereby, homologous recombination of the DNA fragment addressed to a vector side is suppressed. On the other hand, 5'-side of the linearlized vector is digested by 5'→3' exonuclease, and the internal sequence on 3'-side, which become single strand, can be subject to homologous recombination reaction only with the target DNA fragment. As a result, even if the amount of target DNA is one-fifth of that of non-target DNA, only target DNA fragment is introduced into a vector selectively.

A PCR product obtained by using S-oligo DNA (SP1, SP2) as a primer is used as DNA fragment for homologous recombination, and thereby the route B in the FIG. 3 becomes the only reaction route for homologous recombination. In contrast, when a PCR product obtained by using a usual primer is used as DNA fragment for homologous recombination, routes A, B and C in the FIG. 2 become reaction routs for homologous recombination. Among these routes, the route C is the reaction route in which non-target DNA fragment is introduced. The oligo primer used in the present invention is not limited as long as at least one or more bases at 5'-side are resistant to DNA degrading enzymes. It may be an oligo primer whose 5'-side is modified with 2' 4'-BNA.

Homologous Recombination Reaction

The homologous recombination reaction in the present invention may be ET recombination method (Red α/β) or RecE/T system, further be In-Fusion® method.

ET recombination method refers to the homologous recombination reaction conducted in cells with the use of 3'-overhanging end formed by 5'→3' exonuclease digestion with RecE or Red α (referring non-patent publication 1 and patent document 1). The present invention can be performed by using either RecE or Red α. Homologous recombination can be performed by using conventional methods.

In-Fusion® method refers to the homologous recombination reaction conducted in vitro with the use of 5'-overhanging end formed by 5'→3' exonuclease digestion with vaccinia virus DNA polymerase. This reaction requires homologous region of about 15 bp or so between the terminal of DNA fragment and the terminal of a linear vector. When the digestion with 5'→3' exonuclease of vaccinia virus DNA polymerase is reached to the digestion of internal sequence, target DNA fragment is introduced into a vector.

The principle of In-Fusion® method is explained in the article below, and the homologous recombination reagent sold by Takara Bio Inc./Clonetech can be used as is for experiments.

Nucleic Acids Research, 2007, Vol. 35, No. 1 143-151
Michael et. al.
Duplex Strand Joining Reactions Catalyzed by Vaccinia Virus DNA Polymerase A usual homologous recombination reaction using In-Fusion® method is shown in Drawing B of the FIG. 4B. Vaccinia virus DNA polymerase digests 3'-ends of a DNA fragment and a vector. Hereby, a complementary region is appeared between the DNA fragment and the linearlized vector. These complementary chain regions are annealed together to make the DNA fragment be inserted into the vector.

On the other hand, the homologous recombination reaction of the present invention is shown the Drawing A of the FIG. 4. When the digestion with 5'→3' exonuclease of vaccinia virus DNA polymerase is reached to the digestion of internal sequence of PCR product, a complementary chain region between the target DNA fragment (1) and the linearlized vector (1) is appeared. As a result, recombination reaction is occurred. In contrast, the non-target DNA fragment (2) creates a complementary chain region with the vector via a primer sequence, but since there is an internal sequence of the vector which is not homologous to the non-target DNA fragment (2), recombination reaction is not occurred.

Target Gene

A target gene used in the method of the present invention is not particularly limited. The target gene may be for example an antibody gene, and an internal sequence of an amplification primer sequence positioned at one terminal end of a PCR product containing the antibody gene may be a sequence derived from constant region of the antibody gene. Other than antibody gene, the target gene may be T cell receptor gene and a DNA which are for example splicing variants and in which a primer region and internal sequence adjacent thereto are constant but variant site exists internally.

The PCR product is prepared by two times of PCR. The first PCR may be conducted by using an amplification primer containing T1 sequence and an amplification primer containing P3 sequence (provided that the P3 sequence has no homology with any of homologous recombination regions VT1, VP1, VT2 and VP2 of the vector), and the second PCR may be conducted by using an amplification primer containing P1 sequence and an amplification primer containing P2 sequence. The positional relationship of each sequence is shown in the FIG. 5. The P3 sequence is not directly involved in homology recombination, but is used as a primer in the first PCR for nested PCR. The 3' terminal side region of the amplification primer containing P1 sequence and the 5' terminal side region of the amplification primer containing T1 sequence have a sequence which is partially overlapped together, and the amplification primer containing P2 sequence and the amplification primer containing P3 sequence may or may not have a sequence which is partially overlapped together.

It will explain below with an example in which constant region of an immunoglobulin gene is a target gene sequence, by referring the FIG. 6. The primer B (a part thereof) shown in the FIG. 6 corresponds to the primers T1 in the FIGS. 2 and 5, and the primer, D and C correspond to the sequences P1 and P2 in the FIGS. 2 and 5. The primer A of the FIG. 6 corresponds to the primer P3.

(1) PCR Products

Referring to a cDNA synthesis method using magnetic beads shown in the FIG. 6 (immunoglobulin variable region amplification method).

The first PCR is performed by using an immunoglobulin cDNA in which poly dG is attached to the 3'-end of the template (synthesis on magnetic beads), and primers A (constant region of immunoglobulin gene) and B (which is used to bind to poly dG).

After the completion of the first PCR, a diluted sample, for example about 100-times diluted sample, is used as a template for the second PCR. The primers to be used are the primers D and C. The primer D is designed so that the 3'-side sequence of the primer D is overlapped with the 5'-side of the primer B used in the first PCR, and the 3'-terminal side region of the primer D is bond to the 5'-terminal side region of the primer B. The primer C is positioned at the constant region, and is designed to be position inside of the primer A used in the first PCR. In this regards, the primer C may have a sequence which is partially overlapped with the primer A, but may have a sequence which is not overlapped with the primer A. When DNA fragment containing the constant region of immunoglobulin is amplified by the first PCR, with using the primer C and D, the DNA fragment containing the constant region of immunoglobulin can be further amplified. This is one of PCR method called as 5'RACE-PCR (rapid amplification of cDNA end).

The sequence of the primer D+B is an artificial sequence synthesized by the primers B and D in the second PCR reaction, and does not have a sequence specific (inherent) to a template sequence. This portion becomes one of homologous recombination sequences for a vector.

In the second gene amplification reaction, the primer D specifically binds to the 3'-terminal side region of the DNA fragment amplified by the first PCR (because it has a sequence of the primer B), and the primer C binds to the immunoglobulin constant region further inside of the primer A. As a result, specific amplification is performed. In this case, the sequence of D+B surely exists at one side of a PCR product. However, in practice, the used primer binds to a non-target DNA having a sequence similar to the primer, and hereby non specific PCR product may be synthesized. For example, if the primer D non-specifically binds to other DNA fragments, the resulting synthesized DNA fragment has a sequence of the primer D at its end but does not have a sequence of the primer B internally. The DNA fragment having such sequence is not an object of the internal sequence dependent homologous recombination because it does not have the primer D+B sequence (Referring to the vector introducing method by using homologous recombination of immunoglobulin variable region in the FIG. 7). Thus, as shown in the FIG. 5, the sequence of the primer B which is not overlapped with the primer D acts as an internal sequence, and improve the selectivity of homologous recombination of target DNA fragment.

Also, if the primer C binds to a non-target DNA having a nucleotide sequence similar to the primer C and DNA amplification is conducted, the DNA fragment does not have the constant region sequence corresponding to $+\alpha$ shown in the FIG. 7. The sequence corresponding to $+\alpha$ is a sequence specific (inherent) to immunoglobulin chain which is the target DNA. Thus, DNA fragment not having $+\alpha$ as homologous region does not become an object of homologous recombination and is not inserted into a vector (referring to the vector introducing method by using homologous recombination of immunoglobulin variable region in the FIG. 7). Only when the primer C specifically binds to the constant region of immunoglobulin gene which is the target gene and DNA is amplified, the sequence of the primer $C+\alpha$ is appeared on the end of the DNA fragment. This sequence becomes an object of homologous recombination with a vector (FIG. 7).

The method of the present invention is the method in which a PCR product amplified with non-specificity is not introduced into a vector but only PCR product amplified with specificity is automatically introduced into a vector. A prior method requires isolation and purification of specific-amplified product by using gel electrophoresis method or spin column method and others after PCR reaction. Also, gene sequence analysis has to be conducted for the resulting plasmids, and it takes labor and cost.

As described above, the PCR product is prepared by two times of PCR, and the first PCR may be conducted by using an amplification primer containing T1 and P3 sequences, the second PCR may be conducted by using an amplification primer containing P1 and P2 sequences. The amplification primer containing P1 sequence and the amplification primer containing T1 sequence have a sequence which is partially overlapped together in 5'RACE-PCR. The amplification primer containing P2 sequence and the amplification primer containing P3 sequence may or may not have a sequence which is partially overlapped together.

With considering priming capability of PCR, each amplification primer sequence is for example 10 or more bases, preferably in the range of 14 to 35 bases.

The homologous recombination regions derived from the primer sequences P1 and P2 are for example 10 or more bases, preferably in the range of 14 to 35 bases.

The internal sequence T1 and T2 in the inside of the amplification primer sequence which is a nucleotide sequence homologous to a partial sequence of the homologous recombination region is one or more bases, preferably in the range of 5 to 1000 bases. Further, P1+T1 and P2+T2 which is the total with the amplification primer is independently 11 or more bases, preferably in the range of 25 to 1000 bases, respectively.

Cloning Method

The present invention includes a cloning method for a target gene comprising amplification of recombinant DNA molecule in which a PCR product of interest is specifically inserted into a vector (recombinant vector) according to the method of the present invention described above. A conventional method can be used for amplifying a recombinant DNA molecule. The recombinant DNA molecule which is inserted into a vector and is amplified (recombinant vector) can be expressed in cells and the like, and used for obtaining a protein and for functional analysis of the obtained protein. When a gene of interest is an antibody gene, it can be studied whether or not isolated antibody (protein) can bind to an antigen of interest.

Also, a target gene contained in amplified recombinant DNA molecule (recombinant vector) is for example cut off from the vector by restriction enzyme treatment and purified if needed. Isolation and purification of a target gene can be performed by a conventional method. For example, gel extraction or column purification can be listed as isolation and purification of a target gene. Isolated and purified target gene can be used for, for example, nucleotide sequence determination, insertion into an expression vector, and functional analysis of the target gene.

Kit

The present invention also relates to a kit containing a linearlized vector used for homologous recombination method that comprises preparation of a recombinant DNA molecule in which a PCR product, which comprises a target gene sequence, having amplification primer sequences P1 and P2 on its both ends is specifically inserted into a vector.

The linearlized vector contained in the kit has homologous regions VP1 and VP2 comprising nucleotide sequences homologous to amplification primer sequences P1 and P2 of a PCR product, and also has a homologous recombination region VT1 comprising a nucleotide sequence homologous to a sequence T1 which is a part of sequence in the PCR product internal to P1 on the terminal side of VP1 and/or a homologous recombination region VT2 comprising a nucleotide sequence homologous to a sequence T2 which is a part of sequence in the PCR product internal to P2 on the terminal side of VP2. This linearlized vector is the same as that explained in the above "homologous recombination method."

The kit may contain, in addition to the linearlized vector, for example an instruction leaflet for the kit, reagents used for homologous recombination reaction and others. As the reagents used for homologous recombination, for example, reagents for Red (Red α/β) or RecE/T system, reagents for In-Fusion® method and the like are listed.

A homologous recombination method performed by using the present invention kit is, for example, the homologous recombination method of the present invention described above, but it is not limited to that.

Further, a recombinant DNA molecule obtained by the kit of the present invention can be used for a cloning method for a target gene, which method contains amplification of a recombinant having the recombinant DNA molecule.

EXAMPLES

The present invention will be explained below in further details with reference to examples.

Example 1

The advantages of the internal sequence dependent homologous recombination method when a target DNA fragment and a non-target DNA fragment co-exist and are mixed will be shown in Examples 1 to 4 below.

Summary of Experimental Materials

By using primers (a) and (b), two kinds of DNA fragments (1) and (2) were amplified by PCR method.

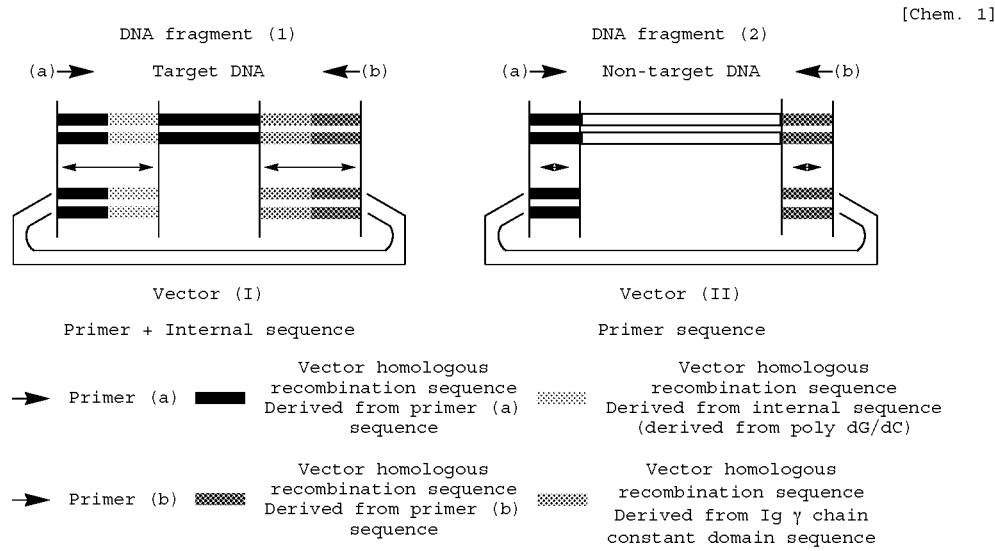

[Chem. 1]

```
Vector (I) homologous recombination sequence:
    primer sequence + internal sequence
    SEQ ID NO: 7
------CTTCGAATTCTGCAGTCGACGGTACCGCGGGGCCGGGATCCCCCCCCGGCCG-3
------GAAGCTTAAGACGTCAGCTGCATGGCCCCCCCCCCCTAGGGGGGGGGGGGGG-5
    SEQ ID NO: 8

SEQ ID NO: 9
5-CGTGGAACTCAGGCGCCCTGACCAGCGGCGTGCACACCTTCCCGGCT------
3-GCACCTTGAGTCCGCGGGACTGGTCGCGGCACGTGTGGAAGGGCCGA------
    SEQ ID NO: 10

Vector (II) homologous recombination sequence: primer sequence
    SEQ ID NO: 11                              SEQ ID NO: 13
----CTTCGAATTCTGCAGTCGACGGTACCGCGGGCCCGGGA-3'    5-CAGCGGCGTGCACACCTTCCCGGCT------
----GAAGCTTAAGACGTCAGGTGCCATGGCGCCCGGGCCCT-5'    3-GTCGCCGCACGTGTGGAAGGGCCGA-------
    SEQ ID NO: 12                              SEQ ID NO: 14
```

The DNA fragment (1) is a target DNA for homologous recombination, and a sequence derived from primer (a) sequence for PCR exists on its end, and further a sequence derived from poly dG/dC sequence exists inside thereof (target DNA side). On another end, a sequence derived from primer (b) sequence exists, and further a sequence derived from human immunoglobulin gamma (Igγ) chain constant region exists inside thereof (target DNA side) (referring the DNA fragment I nucleotide sequence above).

The DNA fragment (2) is a non-target DNA, and a sequence derived from primer (a) sequence for PCR exists on its end, and a sequence derived from primer (b) sequence exists on the other end (referring DNA fragment II nucleotide sequence).

The linear vector (I) has, as homologous recombination region, a sequence derived from primer (a) and poly dG/dC sequence inside thereof, and on the other end a sequence derived from primer (b) and a sequence derived from human immunoglobulin gamma (Igγ) chain constant region inside thereof (referring vector I sequence).

The linear vector (II) has as homologous recombination region a sequence derived from primer (a) and a sequence derived from primer (b) only (referring vector II sequence).

```
Primer(a): (derived from pCMV EGFP N1 multi
cloning site)
                                    (SEQ ID NO. 1)
5'-CTTCGAATTCTGCAGTCGACGGTACCGCGGGCCCGGGA-3'

Primer (b): (derived from human Ig γ chain
constant region)
                                    (SEQ ID NO. 2)
5'-AGCCGGGAAGGTGTGCACGCCGCTG-3
Internal sequence (poly dG/dC)
                                    (SEQ ID NO. 3)
5'-TCCCCCCCCCCCCC-3'
                                    (SEQ ID NO. 4)
3'-AGGGGGGGGGGGGG-5'
Internal sequence (derived from human Ig γ chain
constant region)
                                    (SEQ ID NO. 5)
5'-CGTGGAACTCAGGCGCCCTGAC-3'
                                    (SEQ ID NO. 6)
3'-GCACCTTGAGTCCGCGGGACTG-5'

Vector (I) homologous recombination sequence:
primer sequence (a) + internal sequence
(poly dG/dC)
                                    (SEQ ID NO. 7)
5'-CTTCGAATTCTGCAGTCGACGGTACCGCGGGCCCGGGATCCCCCCCCCC
CCCC-3'
                                    (SEQ ID NO. 8)
3'-GAAGCTTAAGACGTCAGCTGCCATGGCGCCCGGGCCCTAGGGGGGGGG
GGGG-5'

Vector (I) homologous recombination sequence:
internal sequence (derived from human Ig γ chain
constant region) + primer sequence (b)
                                    (SEQ ID NO. 9)
5'-CGTGGAACTCAGGCGCCCTGACCAGCGGCGTGCACACCTTCCCG
GCT-3'
                                    (SEQ ID NO. 10)
3'-GCACCTTGAGTCCGCGGGACTGGTCGCCGCACGTGTGTGGAAGG
GCCGA-5'

Vector (II) homologous recombination sequence:
primer sequence (a)
                                    (SEQ ID NO. 11)
5'-CTTCGAATTCTGCAGTCGACGGTACCGCGGGGCCCGGGA-3'
                                    (SEQ ID NO. 12)
3'-GAAGCTTAAGACGTCAGCTGCCATGGCGCCCGGGCCCT-5'

Vector (II) homologous recombination sequence:
primer sequence (b)
                                    (SEQ ID NO. 13)
5'-CAGCGGCGTGCACACCTTCCCGGCT-3'
                                    (SEQ ID NO. 14)
3'-GTCGCCGCACGTGTGGAAGGGCCGA-5'
```

DNA fragment (1) (FIG. 8, SEQ ID NO. 15) is a target DNA fragment of 683 bp having variable region and a part of constant region of human immunoglobulin gamma chain, and has primer (a) and primer (b) for PCR amplification. It also has, as a sequence used for internal sequence specific homologous recombination reaction, poly dG/dC sequence inside of the primer (a) and a sequence derived from immunoglobulin gamma chain constant region inside of the primer (b) sequence. The positions of the primers (a) and (b) used for amplification are shown by arrows.

DNA fragment (2) (FIG. 9, SEQ ID NO. 16) is a DNA fragment of 628 bp derived from GPF gene, and has primer (a) and primer (b) for PCR amplification on its both ends.

There is no sequence used for internal sequence specific homologous recombination reaction insides of the both primer sequences, and a sequence derived from GFP gene exists.

The sequence of the FIG. 8 was inserted into EcoRI and NotI sites of pCMV EGFPN1 (Clontech) and the vector I (FIG. 10, SEQ ID NO. 17) was prepared. This plasmid has, at the position downstream of EcoRI site, the primer (a) sequence for homologous recombination and poly dG/dC sequence as an internal sequence for specifically inserting human immunoglobulin gamma chain DNA fragment amplified by 5'-RACE PCR. At the position downstream of poly dG/dC sequence, negative selection marker SacB gene (2 kb), which is used for killing *E. coli* having a plasmid not linearized by restriction enzyme digestion on sucrose-containing culture medium, is inserted into EcoRV site (between the positions 62nd and 63rd of SEQ ID NO. 17). At the position downstream of SacB gene, a sequence of human immunoglobulin gamma constant region exists as another internal sequence for specifically inserting human immunoglobulin gamma chain DNA fragment amplified by 5'-RACE PCR. Primer (b) sequence exists downstream of it.

This vector was digested by EcoRV, and then linear plasmid DNA was collected by ethanol-precipitation and prepared at the final concentration of 0.1 μg/μl (FIG. 7).

The sequence of the FIG. 9 was inserted into EcoRI and NotI sites of pCMV EGFPN1 (Clontech) and the vector II (FIG. 11, SEQ ID NO. 18) was prepared. This plasmid has, at the position downstream of EcoRI site, a primer (a) sequence for homologous recombination. At the position downstream of the primer (a) sequence, negative selection marker SacB gene (2 kb), which is used for killing *E. coli* having a plasmid without homologous recombination on sucrose-containing culture medium, is inserted into EcoRV site (between the positions 51st and 52nd of SEQ ID NO. 18). At the position downstream of SacB gene, a primer (b) sequence for homologous recombination exists.

This vector was digested by EcoRV, and then linear plasmid DNA was collected by ethanol-precipitation and prepared at the final concentration of 0.1 μg/μl.

Experiment 1

Homologous Recombination Reaction Using General ET Recombination Method
Method

With using plasmid having DNA fragments 1 and 2 as template, PCR reaction was performed by using primers (a) and (b) and the DNA fragments 1 and 2 were amplified. PCR reaction was performed in 50 μl of reaction system by adding 2 ng of the template plasmid, 10 pmol of each primer and 10 nmol of dNTP and by using PrimeSTAR® heat resistant DNA polymerase (Takara Bio Inc.) and conducting 30 cycles of reaction at 94° C. for 30 seconds-68° C. for 40 seconds. Amplified DNA fragments were purified by spin column method and prepared at the concentration of 50 ng/μl.

Competent cells were prepared according to Red/ET Recombination system (GeneBridges GmbH). 3 μl of the solution in which DNA fragments 1 and 2 and vector (II) were mixed at the ratio of 50 ng:50 ng:100 ng was introduced into *E. coli*. With using the resulting colonies of drug resistant cells, colony PCR method was performed by using primers (a) and (b) and DNA fragment inserted into vector was amplified.

Colony PCR method was performed by suspending *E. coli* colonies into 50 μl of PBS-0.1% Triton X solution and then heating 95° C. for 5 minutes to extract plasmid DNA from cell bodies. PCR reaction was performed by adding 10 pmol of primers (a) and (b) and 10 nmol of dNTP to 1 μl of the above cell body heat extract solution and by conducting reaction in 50 μl of reaction system by using PrimeSTAR® heat resistant DNA polymerase (Takara Bio Inc.) (30 cycles of reaction at 94° C. for 30 seconds-68° C. for 40 seconds). Two (2) μl of the resulting reaction solution was subject to 1% agarose gel electrophoresis and the amplified DNA fragment was isolated.
Results The results of electrophoresis of colony PCR products are shown in the FIG. 12. Six colonies having DNA fragment 1 of 683 bp derived from IgG, five colonies having DNA fragment 2 of 628 bp derived from GFP, and one colony having no DNA fragments 1 or 2 were detected. That is, it became clear that it is difficult for general ET recombination method to insert only target DNA fragment into a vector effectively when target DNA fragment and non-target DNA fragment co-exist and are mixed, Experiment 2

Selective Cloning of Target DNA Using Internal Sequence Dependent Homologous Recombination Reaction
Methods DNA fragments 1 and 2 and vector (I) prepared by Experiment 1 were mixed at the ratio of 50 ng:50 ng:100 ng and 3 μl of the resulting mixed solution was introduced into *E. coli*. With using the resulting colonies of drug resistant cells, DNA fragment inserted into vector (I) was amplified and analyzed with electrophoresis in the same manner as Experiment 1.
Results The results of electrophoresis of colony PCR products are shown in the FIG. 13. Eight colonies having DNA fragment 1 derived from IgG, two colonies having DNA fragment 2 derived from GFP, and two colonies having no DNA fragments 1 or 2 were detected. From these results, it became clear that by using internal sequence dependent homologous recombination reaction target DNA fragment can be inserted into a vector effectively even if target DNA fragment and non-target DNA fragment co-exist and are mixed.

Experiment 3

Internal Sequence Dependent Homologous Recombination Method Using S-oligo Primer With using S-oligo primer in which 3 bases of 5'-terminal of primers (a) and (b) were S-modified, S-modified DNA fragments 1 and 2 were prepared in the same manner as Experiment 1.

These S-modified DNA fragments 1 and 2 and the vector (I) were mixed at the ratio of 50 ng:50 ng:100 ng and 3 μl of the resulting mixed solution was introduced into *E. coli*. With using the resulting colonies of drug resistant cells, colony PCR method was performed by using primers (a) and (b) and DNA fragments inserted into vector were amplified. In the result (FIG. 14), nine colonies having DNA fragment 1 derived from IgG, no colony having DNA fragment 2 derived from GFP, and two colonies having no DNA fragments 1 or 2 were detected.

Experiment 4

S-modified DNA fragments 1 and 2 prepared by Experiment 3 and the vector (I) were mixed at the ratio of 10 ng:50 ng:100 ng and 3 μl of the resulting mixed solution was introduced into *E. coli*. With the same manner, DNA fragments inserted into vector were analyzed. In the result (FIG. 15), seven colonies having DNA fragment 1 derived from IgG, one colony having DNA fragment 2 derived from GFP, and three colonies having no DNA fragments 1 or 2 were detected. From these results, by using PCR products amplified by S-oligo primer and internal sequence dependent homologous recombination reaction, target DNA fragment can be inserted into a vector with 35-folds accuracy.

Experiment 5

Introduction of Human Peripheral Blood B Lymphocyte Immunoglobulin Gamma Chain Variable Region DNA Fragment into Vector Using ET Recombination Method One (1) human peripheral blood B lymphocyte was added to 3 µl of cytolytic solution (100 mM Tris HCl (pH7.5), 500 mM LiCl, 1% lithium dodecyl sulfate (LiDS), 5 mM dithiothreitol) containing 3 µg of magnetic beads (Dynabeads®) to which oligo dT25 bound, and thereby intracellular mRNA bound to the magnetic beads. Then, the magnetic beads were washed with 3 µl of mRNA washing solution A (10 mM Tris HCl (pH7.5), 0.15M LiCl, 0.1% LiDS), followed by 3 µl of mRNA washing solution B (75 mM KCl, 3 mM MgCl$_2$, 0.1% TritonX, 0.5 mM dNTP, 5 mM DTT, 2 unit RNase inhibitor) with one time for each solution. After washing, cDNA synthesis was conducted. That is, 3 µl of cDNA synthesis solution (50 mM Tris HCl (pH8.3), 75 mM KCl, 3 mM MgCl$_2$, 0.1% Triton X-100, 0.5 mM dNTP, 5 mM DTT, 2 unit RNase inhibitor, 10 unit SuperScript III Reverse transcriptase (Invitrogen)) was added to the washed magnetic beads, and reaction was conducted at 50° C. for 1 hour. Next, the magnetic beads was washed with 3 µl of 3' tailing washing solution (50 mM potassium phosphate (pH7.0), 0.5 mM dGTP, 0.1% Triton X-100, 4 mM magnesium chloride) and 3 µl of 3' tailing reaction solution (50 mM potassium phosphate (pH7.0), 0.5 mM dGTP, 0.1% Triton X-100, 4 mM magnesium chloride, terminal deoxynucleotidyl transferase 10U) was added, followed by reaction at 37° C. for 30 minutes.

After the magnetic beads were washed with 3 µl of TE solution (10 mM Tris HCl(pH7.5), 1 mM EDTA, 0.1% TritonX), amplification of human immunoglobulin gamma chain gene was performed by using 5'-RACE PCR method. The first PCR reaction was performed by adding 25 µl of PCR reaction solution (10 pmole of each primer 1 and 2, 10nmol dNTP, PrimeSTAR® heat resistant DNA polymerase (Takara Bio Inc.) 1U) to the magnetic beads and conducting 35 cycles of reaction at 94° C. for 30 seconds-68° C. for 40 seconds. The sequence of primer 1 was 5'-CGGTACCGCGGGCCCGG-GATCCCCCCCCCCCCCDN-3' (SEQ ID NO. 19) and was annealed to the poly dG which was attached to the 3'-terminal of cDNA by terminal deoxynucleotidyl transferase (TdT). The sequence of primer 2 was 5'-ACGCTGCTGAGGGAG-TAGAGTCCTGAG-3' (SEQ ID NO. 20) which was derived from human immunoglobulin gamma chain gene constant region. After the completion of reaction, 225 µl of water was added to the PCR solution and as a template 1 µl of 10-folds diluted solution was subject to PCR reaction by using primer (a) 5'-CTTCGAATTCTGCAGTCGACGGTAC-CGCGGGCCCGGGA-3' (SEQ ID NO. 1) and primer (b) 5'-AGCCGGGAAGGTGTGCACGCCGCTG-3' (SEQ ID NO. 2) under the same condition as the first PCR. The primer (a) was annealed to the region complementary to the primer 1 sequence of the DNA fragment amplified by the first PCR. The primer (b) was derived from human immunoglobulin gamma gene constant region and was positioned upstream of the primer 2 used in the first PCR.

The positional relationship of primers is shown below.

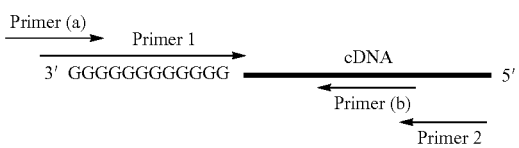

[Chem. 2]

As shown in the FIG. 16, 2 µl of the obtained PCR solution was subject to agarose gel electrophoresis method for separation. In addition to the desired DNA fragment (about 0.8 kb) derived from immunoglobulin gamma chain, DNA fragments derived from non-specific amplification were detected on or around 100-300 bp with smear pattern.

Half (0.5) µl of the PCR reaction solution and 100 ng of vector (I) linearlized by EcoRV digestion were mixed, and 2 µl of the resulting mixture was subject to ET recombination reaction. *E. coli* was grown on kanamycin agar plate containing 0.5% sucrose, and five grown colonies were cultured in 2 ml of LB medium overnight, followed by extraction of plasmid DNA from cells. Plasmid DNA was digested with BamHI/NotI, and introduction efficiency of target human immunoglobulin gamma variable region DNA fragment into vector was studied by agarose gel electrophoresis method. The result (FIG. 17) shows that target DNA fragment was properly inserted into vector in all five colonies analyzed Experiment 6

Internal Sequence Dependent Homologous Recombination Reaction Using In-Fusion® Method DNA fragments 1 and 2 and the vector (I) prepared by Experiment 1 were mixed at the ratio of 50 ng:50 ng:100 ng and 10 µl of the resulting mixed solution was added to In-Fusion® II dry-down reagent (Takara Bio Inc./Clontech), followed by a reaction at 37° C., for 15 minutes. The reaction solution was 5-folds diluted with TE solution, and 2 µl of the diluted solution was introduced into chemical competent cells to be transformed. With using the resulting drug resistant *E. coli* colonies, colony PCR method was performed and DNA fragments inserted in vector were amplified in the same manner as Experiment 1. In the result (FIG. 18-1), seven colonies having DNA fragment 1 derived from IgG, no colony having DNA fragment 2 derived from GFP, and four colonies having no DNA fragments 1 or 2 were detected. These results show that internal sequence dependent homologous recombination method is a technique applicable to not only ET recombination method but also In-Fusion® method.

Experiment 7

Introduction of Human Peripheral Blood B Lymphocyte Immunoglobulin Gamma Chain Variable Region DNA Fragment into Vector Using In-Fusion® Method Target human immunoglobulin gamma chain variable region DNA fragment prepared by Experiment 5 and vector (I) were mixed at the ratio of 50 ng:100 ng, and 10 µl of the resulting mixture was added to In-Fusion® II dry-down reagent (Takara Bio Inc./Clontech), and then subject to a reaction at 37° C., for 15 minutes, followed by at 50° C., for 15 minutes. The reaction solution was 5-folds diluted with TE solution, and 2 µl of the diluted solution was introduced into chemical competent cells to be transformed. With using the resulting drug resistant *E. coli* colonies, plasmid DNA was extracted in the same manner as Experiment 5. Plasmid DNA was digested with BamHI/NotI, and introduction efficiency of target human immunoglobulin gamma chain variable region DNA fragment into vector was studied by agarose gel electrophoresis method. The result (FIG. 18-2) shows that target immunoglobulin gene fragment was properly inserted into vector in all twelve colonies analyzed. These results demonstrated that the present invention also provides specific introduction of a PCR product of interest into vector in In-Fusion® method which employs different reaction mechanism in homologous recombination from that of ET recombination method.

Example 2

Preparation of DNA Fragment

DNA fragment I used in Experiment 1 was used as a template, and PCR was performed by using primer 1 (5'-CGG-TACCGCGGGCCCGGGATCCCCCCCCCCCCDN-3') (SEQ ID NO. 19) and other primers (b) to (e) below, respectively. PCR reaction condition followed that of Experiment 1.

The positional relationship of each primer below and DNA fragment 1 is shown in the FIG. 19.

```
Primer (b)
5'-AGCCGGGAAGGTGTGCACGCCGCTG-3'      (SEQ ID NO. 21)

Primer (c)
5'-AGGTGTGCACGCCGCTGGTC-3'           ((SEQ ID NO. 22)

Primer (d)
5'-CACGCCGCTGGTCAGGGCGCCTG-3'        ((SEQ ID NO. 23)

Primer (e)
5'-CTGGTCAGGGCGCCTGAGTTCCA-3'        (SEQ ID NO. 24)
```

The sample after PCR was purified by spin column method, and 1 μl of the resulting solution was analyzed by agarose gel electrophoresis. In the results, DNA fragments having expected size were observed (FIG. 20). 100 ng of vector (I) prepared by Experiment 1 and 25 ng of each DNA fragment were mixed, and 2 μl of the mixture was subject to homologous recombination reaction using Rec/ET recombination method. *E. coli* was grown on kanamycin agar plate containing 0.5% sucrose and the number of grown colonies was studies. The number of resulting colonies were 146 colonies (DNA fragment 1-b), 125 colonies (DNA fragment 1-(c)), 144 colonies (DNA fragment 1-(d)), and 80 colonies (DNA fragment 1-e).

Five (5) grown colonies were cultured in 2 ml of LB medium overnight, followed by extraction of plasmid DNA from cells. Plasmid DNA was digested with BamHI/NotI, and introduction efficiency of each DNA fragment into vector was studied by agarose gel electrophoresis method (FIG. 21). The plasmid having target DNA fragment is detected as full-length human immunoglobulin gamma chain (about 1.5 kb) and vector (about 4 kb) by BamHI/NotI digestion.

The results (FIG. 21) show that DNA fragment of interest was introduced into vector by the ratio of 100% with using DNA fragment 1-(b), 80% with DNA fragment 1-(c) or 1-(d), and 60% with DNA fragment 1-(e). It became clear from the these results that internal sequence dependent homologous recombination requires an internal sequence having at least two or more bases on one side and in addition 25 or more bases in total of the internal sequence and amplification primer sequence. The map of homologous recombination regions of each DNA fragment and vector is shown in the FIG. 22.

Industrial Applicability

The present invention is useful to gene technology area.

Brief Description of Drawings

FIG. 4 is an explanatory diagram showing reaction mechanisms of a general homologous recombination reaction (B) and the homologous recombination reaction of the present invention (A) by using In-Fusion® method (Experiment 6 of Example 1).

FIG. 8 shows the nucleotide sequence of DNA fragment (1) (SEQ ID NO. 15) used in Example 1.

FIG. 9 shoes the nucleotide sequence of DNA fragment (2) (SEQ ID NO. 16) used in Example 1.

FIG. 10 shows the nucleotide sequence of vector I (SEQ ID NO. 17) used in Example 1.

FIG. 11 shows the nucleotide sequence of vector II (SEQ ID NO. 18) used in Example 1.

FIG. 18-1 shows the results of electrophoresis of colony PCR products in Experiment 6 of Example 1.

FIG. 18-2 shows the results of agarose gel electrophoresis in Experiment 7 of Example 1.

FIG. 20 shows the results of agarose gel electrophoresis of the samples after PCR (purified by spin column method) in Example 2.

FIG. 21 shows the results of agarose gel electrophoresis of plasmid DNA digested by BamHI/NotI in Example 2.

SEQUENCE LISTING

<160> NUMBER OF SEQ ID NOS: 24

Figure 1:
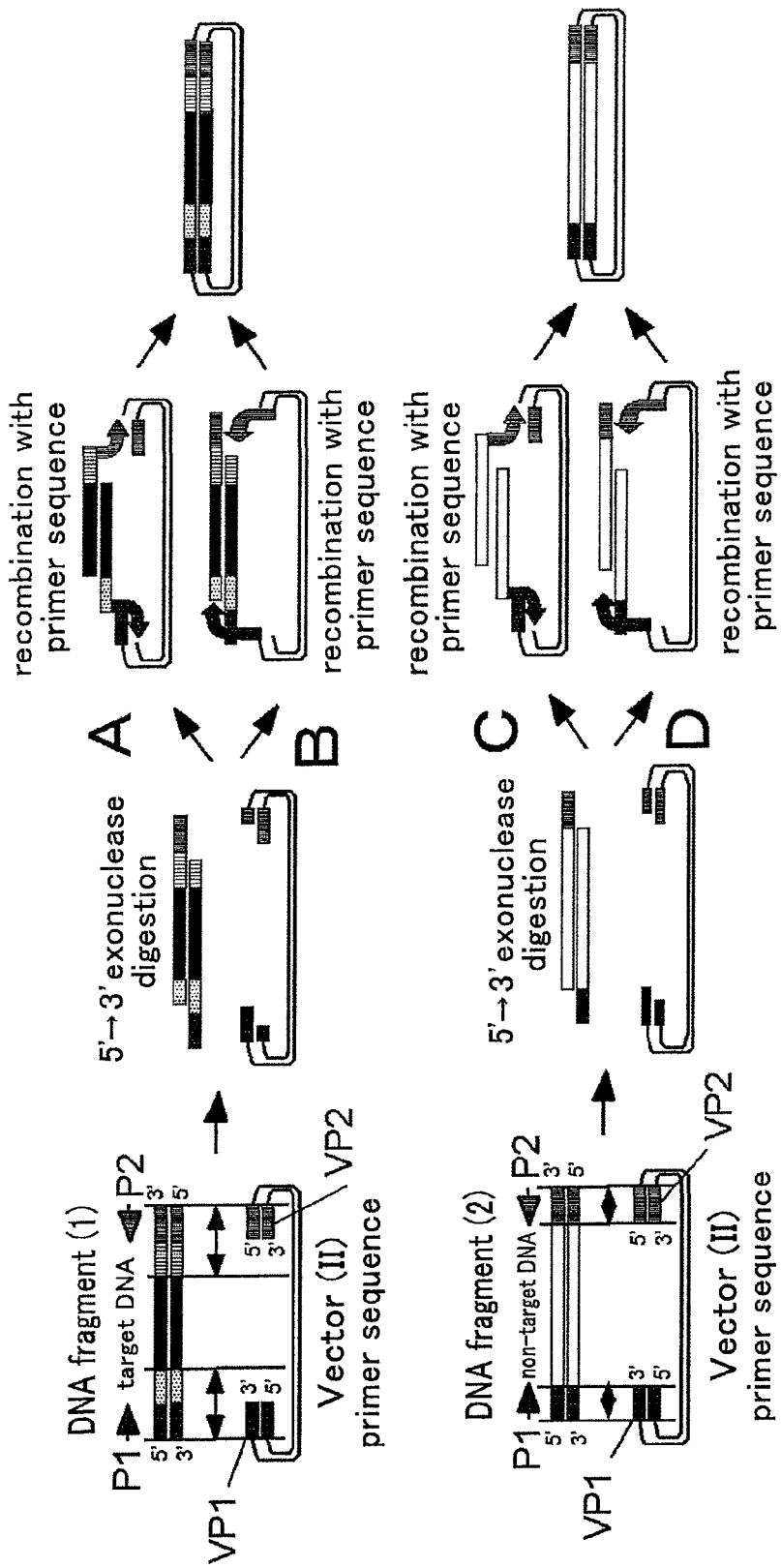
FIG. 1 is an explanatory diagram showing reaction mechanism of a general homologous recombination method (Experiment 1).
Figure 2:
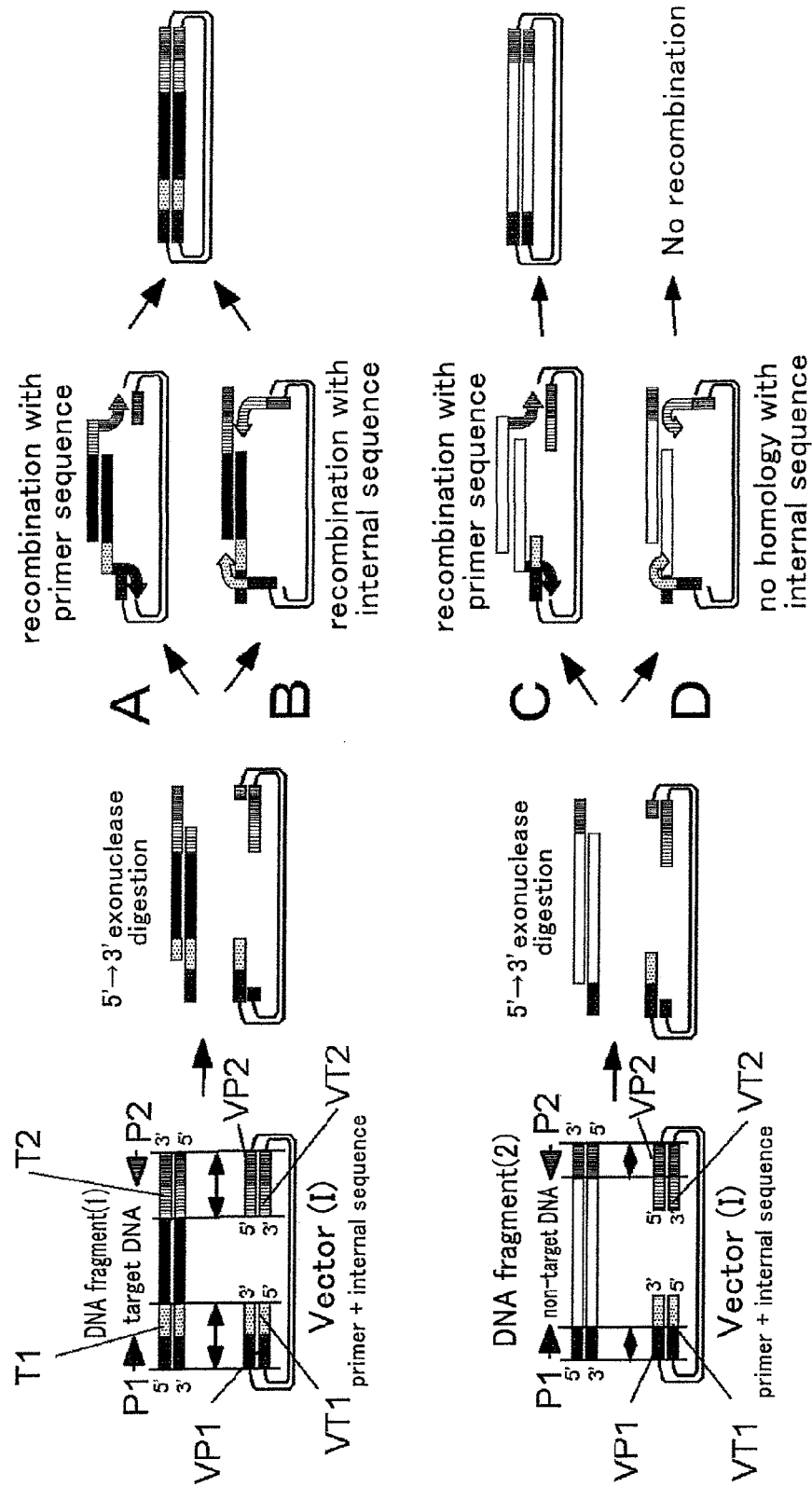
FIG. 2 is an explanatory diagram showing reaction mechanism of internal sequence dependent homologous recombination method (Experiment 2).
Figure 3:
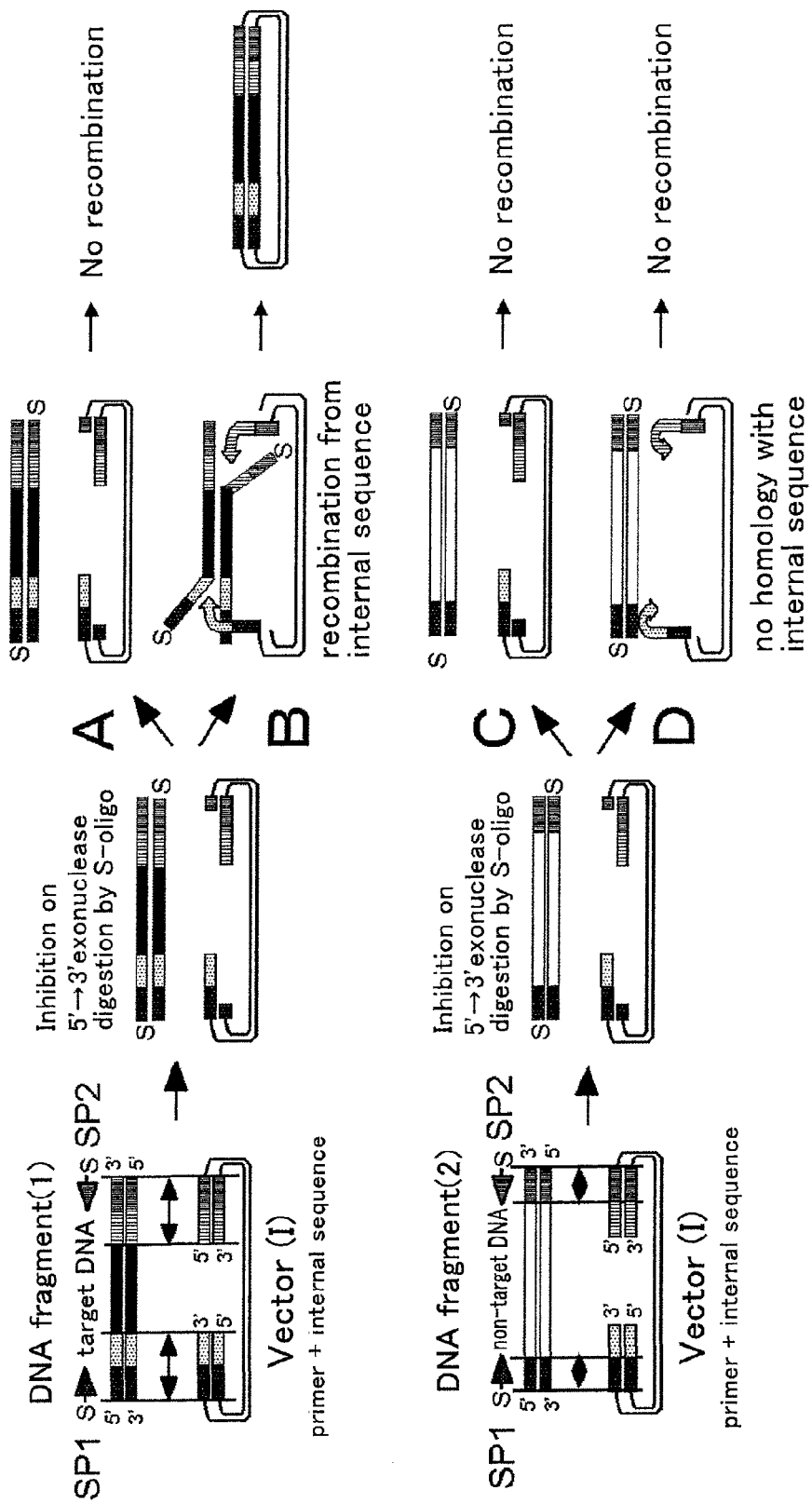
FIG. 3 is an explanatory diagram showing reaction mechanism of internal sequence dependent homologous recombination method using S-oligo primer (Experiment 3 of Example 1).
Figure 5:
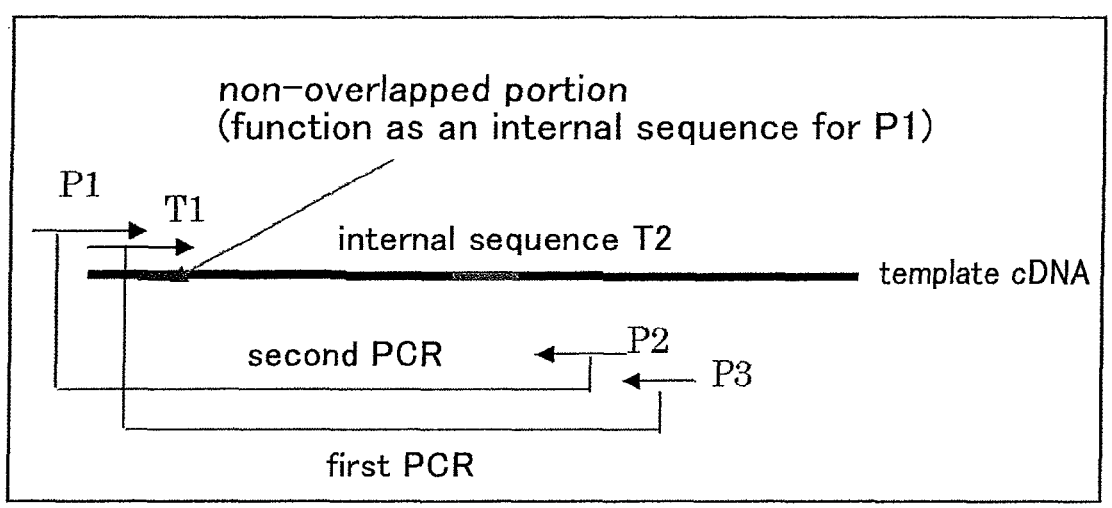
FIG. 5 is an explanatory diagram showing preparation of PCR products by two times of PCR.
Figure 6:
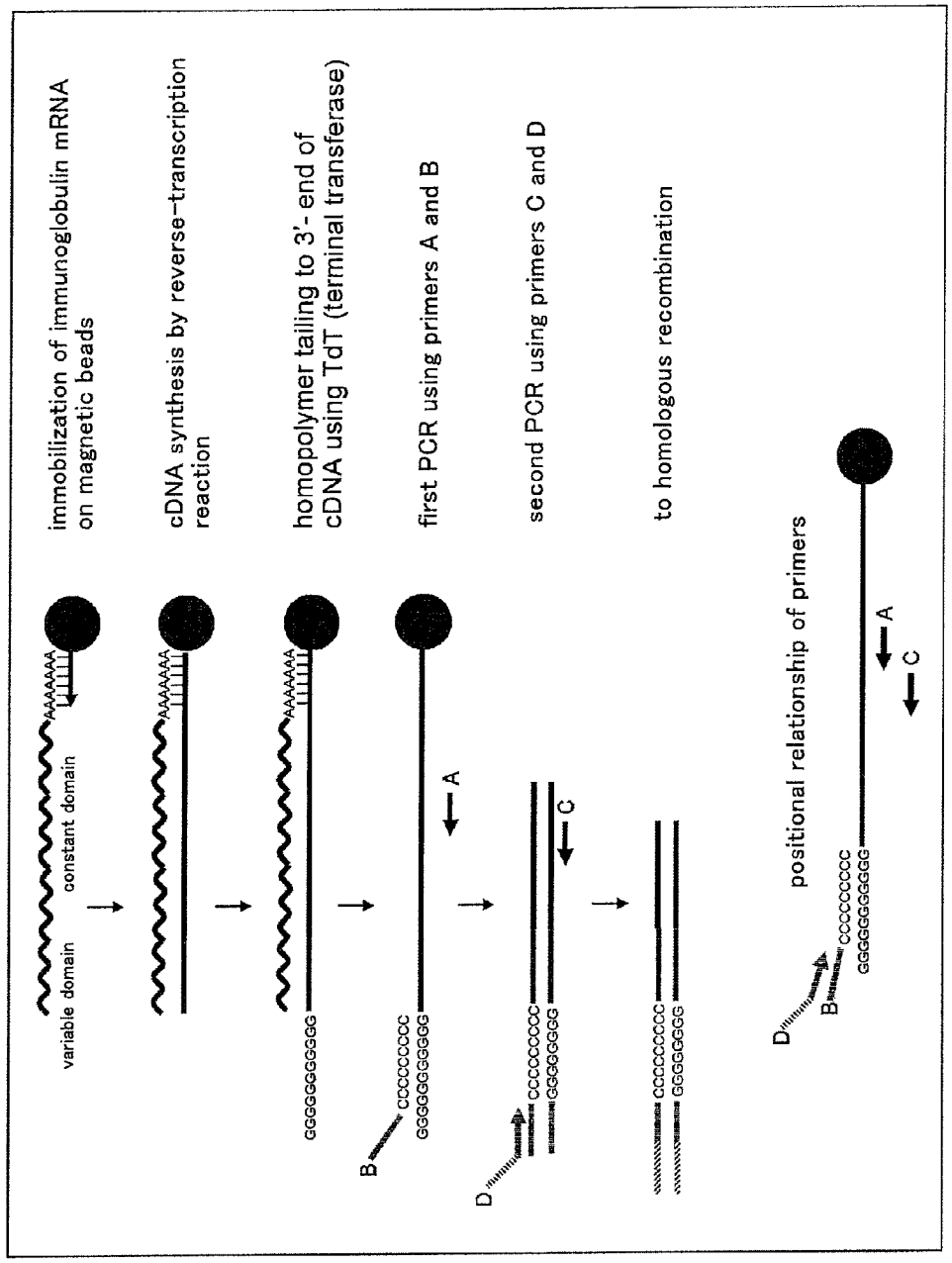
FIG. 6 is an explanatory diagram showing cDNA synthesis method using magnetic beads (immunoglobulin variable region amplification method).
Figure 7:
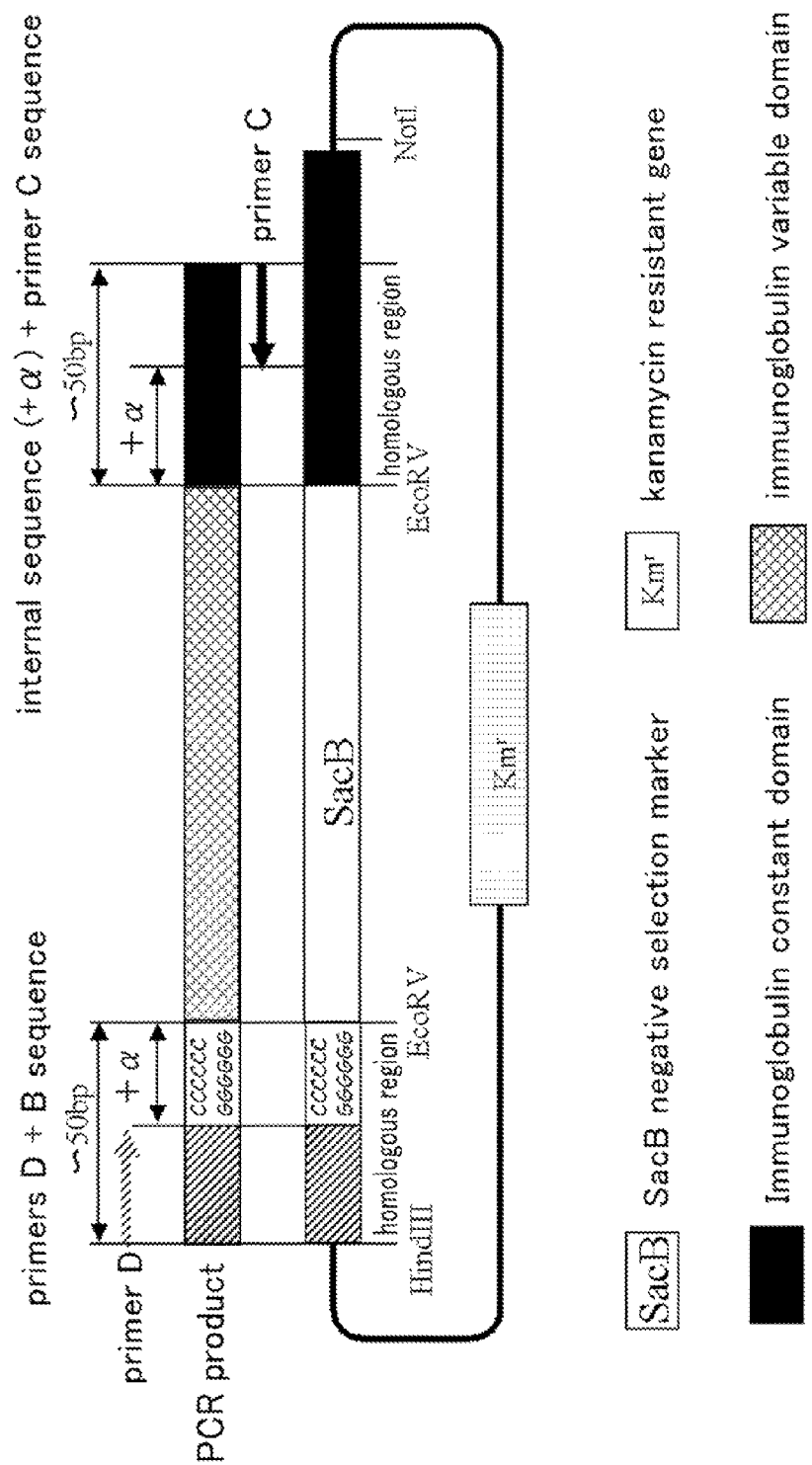
FIG. 7 is an explanatory diagram showing a method for vector introduction using homologous recombination of human immunoglobulin variable region.
Figure 12:
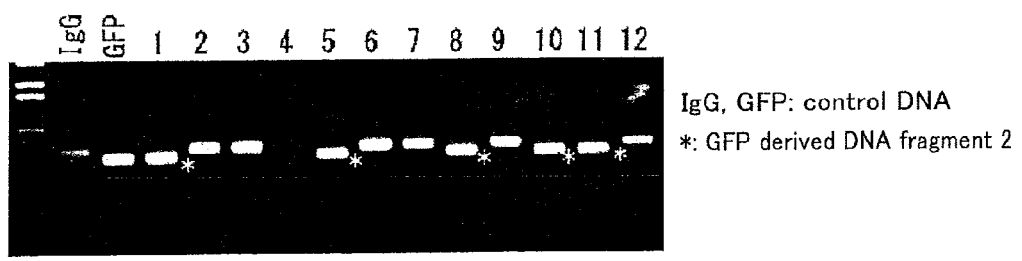
FIG. 12 shows the results of electrophoresis of colony PCR products in Experiment 1 of Example 1.
Figure 13:
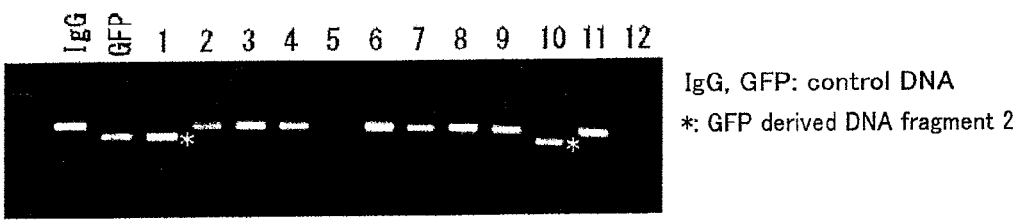
FIG. 13 shows the results of electrophoresis of colony PCR products in Experiment 2 of Example 1.
Figure 14:
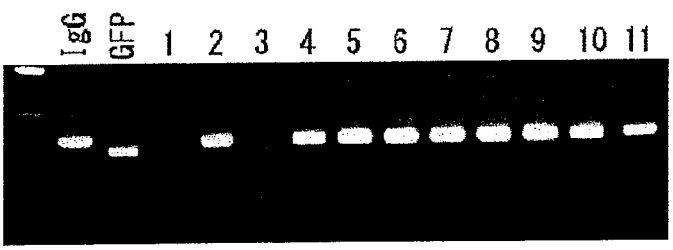
FIG. 14 shows the results of electrophoresis of colony PCR products in Experiment 3 of Example 1.
Figure 15:
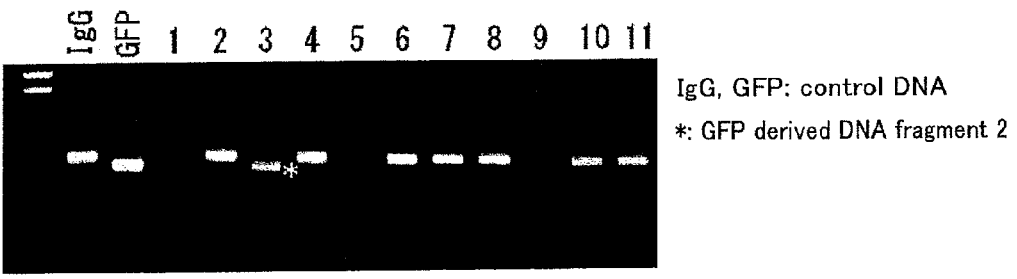
FIG. 15 shows the results of electrophoresis of colony PCR products in Experiment 4 of Example 1.
Figure 16:
FIG. 16 shows the results of agarose gel electrophoresis of PCR reaction solution in Experiment 5 of Example 1.
Figure 17:
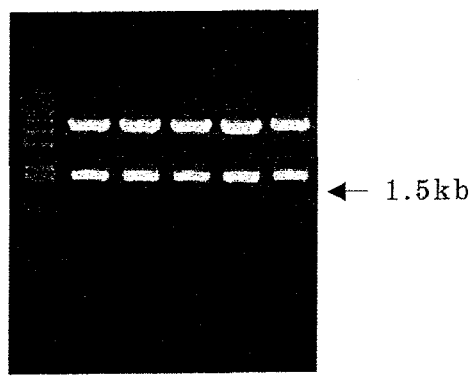
FIG. 17 shows the results of agarose gel electrophoresis of plasmid DNA digested by BamHI/NotI in Experiment 5 of Example 1. The plasmid having target DNA fragment is detected as full-length human immunoglobulin gamma chain (about 1.5 kb) and vector (about 4 kb) by BamHI/NotI digestion. When the PCR-amplified human immunoglobulin gamma variable region is not inserted, human immunoglobulin gamma chain constant region (about 0.8 kb) and vector (about 4 kb) are detected by BamHI/NotI digestion.
Figures 1, 18:
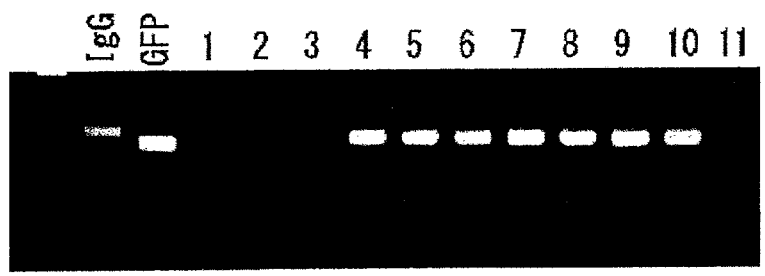
Figures 2, 18:
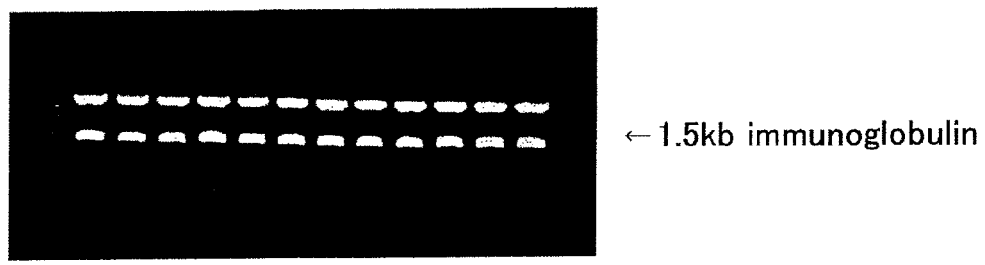
Figure 19:
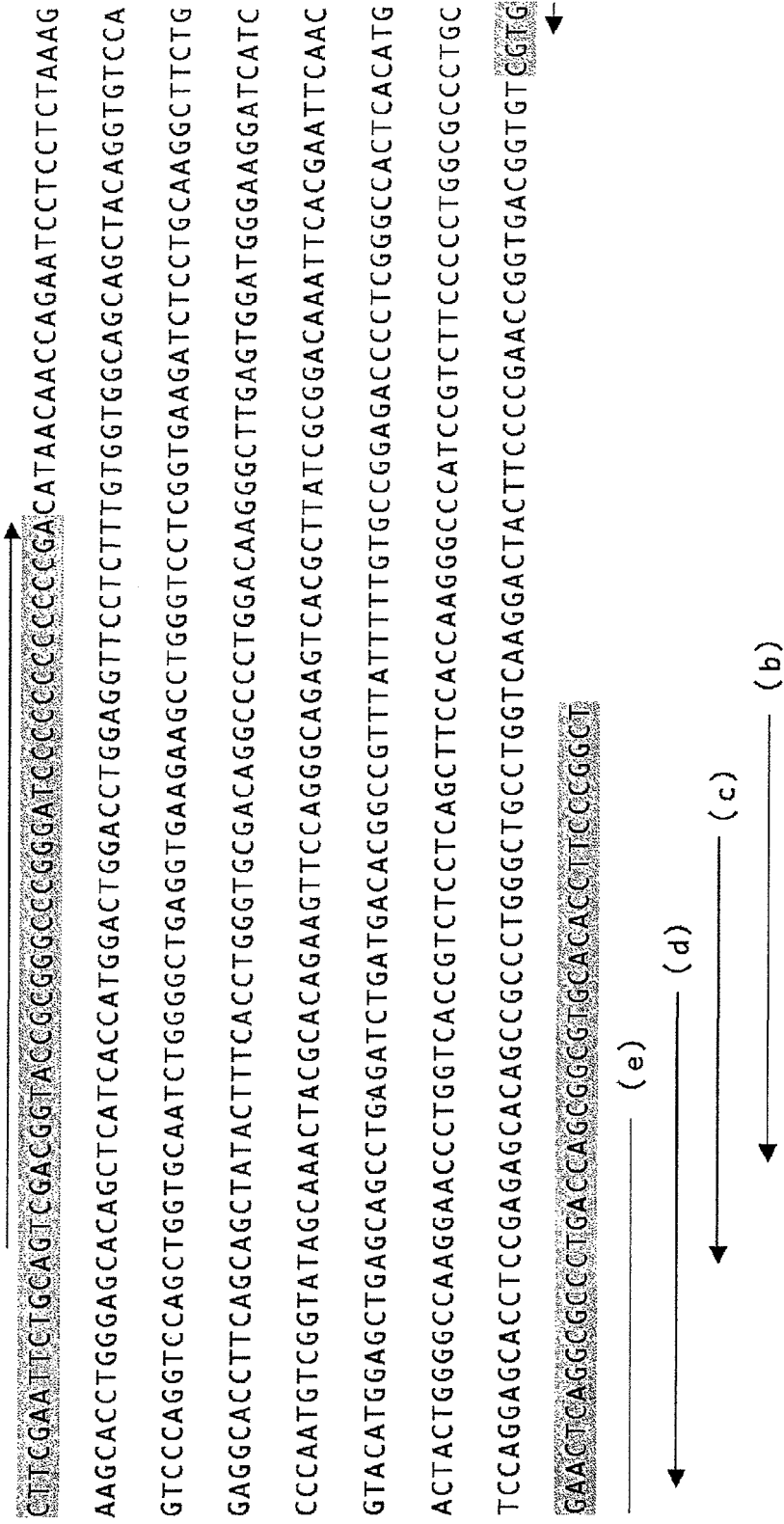
FIG. 19 shows the positional relationship of primer sequences and DNA fragment 1 used in Example 2.
Figure 22:
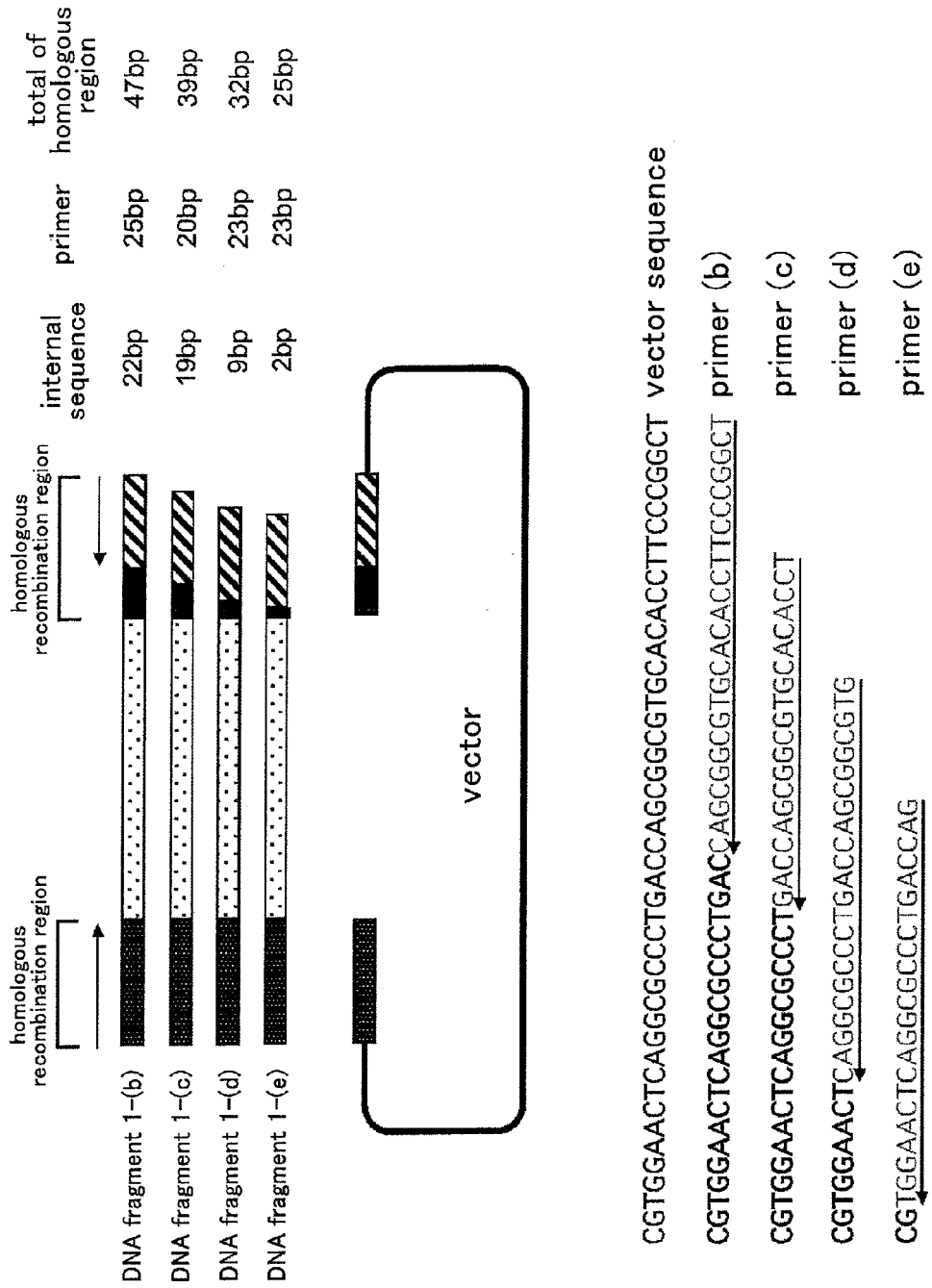
FIG. 22 is a diagram showing homologous recombination regions of each DNA fragment and vector in Example 2.

<210> SEQ ID NO 1
<211> LENGTH: 38
<212> TYPE: DNA
<213> ORGANISM: Artificial sequence
<220> FEATURE:
<223> OTHER INFORMATION: Primer

<400> SEQUENCE: 1
cttcgaattc tgcagtcgac ggtaccgcgg gcccggga                    38

<210> SEQ ID NO 2
<211> LENGTH: 25
<212> TYPE: DNA
<213> ORGANISM: Artificial sequence
<220> FEATURE:
<223> OTHER INFORMATION: Primer

<400> SEQUENCE: 2
agccgggaag gtgtgcacgc cgctg                                  25

<210> SEQ ID NO 3
<211> LENGTH: 14
<212> TYPE: DNA
<213> ORGANISM: Artificial sequence
<220> FEATURE:
<223> OTHER INFORMATION: Internal sequence

<400> SEQUENCE: 3 tcccccccccc cccc                                             14

<210> SEQ ID NO 4
<211> LENGTH: 14
<212> TYPE: DNA
<213> ORGANISM: Artificial sequence
<220> FEATURE:
<223> OTHER INFORMATION: Internal sequence

<400> SEQUENCE: 4
gggggggggg ggga                                              14

<210> SEQ ID NO 5
<211> LENGTH: 22
<212> TYPE: DNA
<213> ORGANISM: Artificial sequence
<220> FEATURE:
<223> OTHER INFORMATION: Internal sequence

<400> SEQUENCE: 5
cgtggaactc aggcgccctg ac                                     22

<210> SEQ ID NO 6
<211> LENGTH: 22
<212> TYPE: DNA
<213> ORGANISM: Artificial sequence
<220> FEATURE:
<223> OTHER INFORMATION: Internal sequence

<400> SEQUENCE: 6
gtcagggcgc ctgagttcca cg                                     22

<210> SEQ ID NO 7
<211> LENGTH: 52
<212> TYPE: DNA
<213> ORGANISM: Artificial sequence

```
<220> FEATURE:
<223> OTHER INFORMATION: misc_recomb

<400> SEQUENCE: 7
cttcgaattc tgcagtcgac ggtaccgcgg gcccgggatc cccccccccc cc            52

<210> SEQ ID NO 8
<211> LENGTH: 52
<212> TYPE: DNA
<213> ORGANISM: Artificial sequence
<220> FEATURE:
<223> OTHER INFORMATION: misc_recomb

<400> SEQUENCE: 8
gggggggggg gggatcccgg gcccgcggta ccgtcgactg cagaattcga ag            52

<210> SEQ ID NO 9
<211> LENGTH: 47
<212> TYPE: DNA
<213> ORGANISM: Artificial sequence
<220> FEATURE:
<223> OTHER INFORMATION: misc_recomb

<400> SEQUENCE: 9
cgtggaactc aggcgccctg accagcggcg tgcacacctt cccggct                  47

<210> SEQ ID NO 10
<211> LENGTH: 47
<212> TYPE: DNA
<213> ORGANISM: Artificial sequence
<220> FEATURE:
<223> OTHER INFORMATION: misc_recomb

<400> SEQUENCE: 10
agccgggaag gtgtgcacgc cgctggtcag ggcgcctgag ttccacg                  47

<210> SEQ ID NO 11
<211> LENGTH: 38
<212> TYPE: DNA
<213> ORGANISM: Artificial sequence
<220> FEATURE:
<223> OTHER INFORMATION: misc_recomb

<400> SEQUENCE: 11
cttcgaattc tgcagtcgac ggtaccgcgg gcccggga                            38

<210> SEQ ID NO 12
<211> LENGTH: 38
<212> TYPE: DNA
<213> ORGANISM: Artificial sequence
<220> FEATURE:
<223> OTHER INFORMATION: misc_recomb

<400> SEQUENCE: 12
tcccgggccc gcggtaccgt cgactgcaga attcgaag                            38

<210> SEQ ID NO 13
<211> LENGTH: 25
<212> TYPE: DNA
<213> ORGANISM: Artificial sequence
<220> FEATURE:
<223> OTHER INFORMATION: misc_recomb

<400> SEQUENCE: 13
cagcggcgtg cacaccttcc cggct                                          25
```

<210> SEQ ID NO 14
<211> LENGTH: 25
<212> TYPE: DNA
<213> ORGANISM: Artificial sequence
<220> FEATURE:
<223> OTHER INFORMATION: misc_recomb

<400> SEQUENCE: 14
agccgggaag gtgtgcacgc cgctg                                          25

<210> SEQ ID NO 15
<211> LENGTH: 683
<212> TYPE: DNA
<213> ORGANISM: Artificial sequence
<220> FEATURE:
<223> OTHER INFORMATION: DNA fragment

<400> SEQUENCE: 15
cttcgaattc tgcagtcgac ggtaccgcgg gcccgggatc ccccccccc cgacataaca      60 accagaatcc tcctctaaag aagcacctgg gagcacagct catcaccatg gactggacct    120
ggaggttcct ctttgtggtg gcagcagcta caggtgtcca gtcccaggtc cagctggtgc    180
aatctggggc tgaggtgaag aagcctgggt cctcggtgaa gatctcctgc aaggcttctg    240
gaggcacctt cagcagctat actttcacct gggtgcgaca ggcccctgga caagggcttg    300
agtggatggg aaggatcatc cccaatgtcg gtatagcaaa ctacgcacag aagttccagg    360
gcagagtcac gcttatcgcg gacaaattca cgaattcaac gtacatggag ctgagcagcc    420
tgagatctga tgacacggcc gtttattttt gtgccggaga ccccctcggc cactcacatg    480
actactgggg ccaaggaacc ctggtcaccg tctcctcagc ttccaccaag gcccatccg     540 tcttcccccct ggcgccctgc tccaggagca cctccgagag cacagccgcc ctgggctgcc    600
tggtcaagga ctacttcccc gaaccggtga cggtgtcgtg gaactcaggc gccctgacca    660
gcggcgtgca caccttcccg gct                                           683

<210> SEQ ID NO 16
<211> LENGTH: 628
<212> TYPE: DNA
<213> ORGANISM: Artificial sequence
<220> FEATURE:
<223> OTHER INFORMATION: DNA fragment

<400> SEQUENCE: 16
cttcgaattc tgcagtcgac ggtaccgcgg gcccgggatc caccggtcgc caccatggtg     60
agcaagggcg aggagctgtt caccggggtg gtgcccatcc tggtcgagct ggacggcgac    120
gtaaacggcc acaagttcag cgtgtccggc gagggcgagg gcgatgccac ctacggcaag    180
ctgaccctga agttcatctg caccaccggc aagctgcccg tgccctggcc caccctcgtg    240 accacccctga cctacggcgt gcagtgcttc agccgctacc ccgaccacat gaagcagcac    300
gacttcttca gtccgccat gcccgaaggc tacgtccagg agcgcaccat cttcttcaag    360
gacgacggca actacaagac ccgcgccgag gtgaagttcg agggcgacac cctggtgaac    420
cgcatcgagc tgaagggcat cgacttcaag gaggacggca acatcctggg gcacaagctg    480
gagtacaact acaacagcca caacgtctat atcatggccg acaagcagaa gaacggcatc    540
aaggtgaact tcaagatccg ccacaacatc gaggacggca gcgtgcagct cgccgaccac    600
taccagcggc gtgcacacct tcccggct                                     628

<210> SEQ ID NO 17
<211> LENGTH: 2856
<212> TYPE: DNA
<213> ORGANISM: Artificial sequence
<220> FEATURE:
<223> OTHER INFORMATION: Vector DNA

<400> SEQUENCE: 17

```
aagcttcgaa ttctgcagtc gacggtaccg cgggcccggg atcccccccc ccccgatat      60 cgatccgacg tccacatata cctgccgttc actattattt agtgaaatga gatattatga     120
tattttctga attgtgatta aaaaggcaac tttatgccca tgcaacagaa actataaaaa     180
atacagagaa tgaaaagaaa cagatagatt ttttagttct ttaggcccgt agtctgcaaa     240
tccttttatg attttctatc aaacaaaaga ggaaaataga ccagttgcaa tccaaacgag     300
agtctaatag aatgaggtcg aaaagtaaat cgcgcgggtt tgttactgat aaagcaggca     360
agacctaaaa tgtgtaaagg gcaaagtgta tactttggcg tcaccccta catattttag      420 gtctttttt attgtgcgta actaacttgc catcttcaaa caggagggct ggaagaagca      480
gaccgctaac acagtacata aaaaggaga catgaacgat gaacatcaaa agtttgcaa      540 aacaagcaac agtattaacc tttactaccg cactgctggc aggaggcgca actcaagcgt     600 tgcgaaaga acgaaccaa aagccatata aggaaacata cggcatttcc catattacac      660
gccatgatat gctgcaaatc cctgaacagc aaaaaaatga aaatatcaa gttcctgagt      720 tcgattcgtc cacaattaaa aatatctctt ctgcaaaagg cctggacgtt tgggacagct     780
ggccattaca aaacgctgac ggcactgtcg caaactatca cggctaccac atcgtctttg    840
cattagccgg agatcctaaa atgcggatg acacatcgat ttacatgttc tatcaaaaag    900
tcggcgaaac ttctattgac agctggaaaa acgctggccg cgtctttaaa gacagcgaca    960
aattcgatgc aaatgattct atcctaaaag accaaacaca gaatggtca ggttcagcca    1020 catttacatc tgacggaaaa atccgtttat tctacactga tttctccggt aaacattacg    1080
gcaaacaaac actgacaact gcacaagtta acgtatcagc atcagacagc tctttgaaca    1140
tcaacggtgt agaggattat aaatcaatct ttgacggtga cggaaaaacg tatcaaaatg    1200
tacagcagtt catcgatgaa ggcaactaca gctcaggcga caaccatacg ctgagagatc    1260
ctcactacgt agaagataaa ggccacaat acttagtatt tgaagcaaac actggaactg    1320
aagatggcta ccaaggcgaa gaatctttat ttaacaaagc atactatggc aaaagcacat    1380
cattcttccg tcaagaaagt caaaaacttc tgcaaagcga taaaaaacgc acggctgagt    1440
tagcaaacgc cgctctcggt atgattgagc taaacgatga ttacacactg aaaaaagtga    1500
tgaaaccgct gattgcatct aacacagtaa cagatgaaat tgaacgcgcg aacgtctttta    1560 aaatgaacgg caaatggtac ctgttcactg actcccgcgg atcaaaaatg acgattgacg    1620
gcattacgtc taacgatatt tacatgcttg gttatgtttc taattcttta actggcccat    1680
acaagccgct gaacaaaact ggccttgtgt taaaaatgga tcttgatcct aacgatgtaa    1740
cctttactta ctcacacttc gctgtacctc aagcgaaagg aaacaatgtc gtgattacaa    1800
gctatatgac aaacagagga ttctacgcag acaaacaatc aacgtttgcg cctagcttcc    1860
tgctgaacat caaaggcaag aaaacatctg ttgtcaaaga cagcatcctt gaacaaggac    1920
aattaacagt taacaaataa aaacgcaaaa gaaaatgccg atatccgtgg aactcaggcg    1980
ccctgaccag cggcgtgcac accttccgg ctgtcctaca gtcctcagga ctctactccc    2040
tcagcagcgt ggtgaccgtg ccctccagca gcttgggcac ccagacctac acctgcaacg    2100
```

| | |
|---|---|
| tgaatcacaa gcccagcaac accaaggtgg acaagagagt tgagcccaaa tcttgtgaca | 2160 |
| aaactcacac atgcccaccg tgcccagcac ctgaactcct ggggggaccg tcagtcttcc | 2220 |
| tcttccccc aaaacccaag gacaccctca tgatctcccg gacccctgag gtcacatgcg | 2280 |
| tggtggtgga cgtgagccac gaagaccctg aggtcaagtt caactggtac gtggacggcg | 2340 |
| tggaggtgca taatgccaag acaaagccgc gggaggagca gtacaacagc acgtaccgtg | 2400 |
| tggtcagcgt cctcaccgtc ctgcaccagg actggctgaa tggcaaggag tacaagtgca | 2460 |
| aggtctccaa caaagccctc ccagccccca tcgagaaaac catctccaaa gccaaagggc | 2520 |
| agccccgaga accacaggtg tacaccctgc cccatcccg ggatgagctg accaagaacc | 2580 |
| aggtcagcct gacctgcctg gtcaaaggct tctatcccag cgacatcgcc gtggagtggg | 2640 |
| agagcaatgg gcagccggag aacaactaca agaccacgcc tcccgtgctg gactccgacg | 2700 |
| gctccttctt cctctacagc aagctcaccg tggacaagag caggtggcag caggggaacg | 2760 |
| tcttctcatg ctccgtgatg catgagggtc tgcacaacca ctacacgcag aagagcctct | 2820 |
| ccctgtctcc gggtaaatga gtgcgacggc ggccgc | 2856 |

<210> SEQ ID NO 18
<211> LENGTH: 2823
<212> TYPE: DNA
<213> ORGANISM: Artificial sequence
<220> FEATURE:
<223> OTHER INFORMATION: Vector DNA
<400> SEQUENCE: 18

| | |
|---|---|
| aagcttcgaa ttctgcagtc gacggtaccg cgggcccggg atccgatatc gatccgacgt | 60 |
| ccacatatac ctgccgttca ctattattta gtgaaatgag atattatgat attttctgaa | 120 |
| ttgtgattaa aaaggcaact ttatgcccat gcaacagaaa ctataaaaaa tacagagaat | 180 |
| gaaaagaaac agatagattt tttagttctt taggcccgta gtctgcaaat ccttttatga | 240 |
| ttttctatca acaaaagag gaaaatagac cagttgcaat ccaaacgaga gtctaataga | 300 |
| atgaggtcga aaagtaaatc gcgcgggttt gttactgata aagcaggcaa gacctaaaat | 360 |
| gtgtaaaggg caaagtgtat actttggcgt caccccttac atattttagg tcttttttta | 420 |
| ttgtgcgtaa ctaacttgcc atcttcaaac aggagggctg aagaagcag accgctaaca | 480 |
| cagtacataa aaaggagac atgaacgatg aacatcaaaa agtttgcaaa acaagcaaca | 540 |
| gtattaacct ttactaccgc actgctggca ggaggcgcaa ctcaagcgtt tgcgaaagaa | 600 |
| acgaaccaaa agccatataa ggaaacatac ggcatttccc atattacacg ccatgatatg | 660 |
| ctgcaaatcc ctgaacagca aaaaatgaa aaatatcaag ttcctgagtt cgattcgtcc | 720 |
| acaattaaaa atatctcttc tgcaaaaggc ctggacgttt gggacagctg gccattacaa | 780 |
| aacgctgacg gcactgtcgc aaactatcac ggctaccaca tcgtctttgc attagccgga | 840 |
| gatcctaaaa atgcggatga cacatcgatt tacatgttct atcaaaaagt cggcgaaact | 900 |
| tctattgaca gctggaaaaa cgctggccgc gtctttaaag acagcgacaa attcgatgca | 960 |
| aatgattcta tcctaaaaga ccaaacacaa gaatggtcag gttcagccac atttacatct | 1020 |
| gacggaaaaa tccgttttat tctacactgat ttctccggta acattacgg caaacaaaca | 1080 |
| ctgacaactg cacaagttaa cgtatcagca tcagacagct ctttgaacat caacggtgta | 1140 |
| gaggattata atcaatctt tgacggtgac ggaaaaacgt atcaaaatgt acagcagttc | 1200 |
| atcgatgaag caactacag ctcaggcgac aaccatacgc tgagagatcc tcactacgta | 1260 |
| gaagataaag gccacaaata cttagtattt gaagcaaaca ctggaactga agatggctac | 1320 |

```
caaggcgaag aatctttatt taacaaagca tactatggca aaagcacatc attcttccgt    1380
caagaaagtc aaaaacttct gcaaagcgat aaaaaacgca cggctgagtt agcaaacggc    1440
gctctcggta tgattgagct aaacgatgat tacacactga aaaaagtgat gaaaccgctg    1500
attgcatcta acacagtaac agatgaaatt gaacgcgcgc acgtctttaa aatgaacggc    1560
aaatggtacc tgttcactga ctcccgcgga tcaaaaatga cgattgacgg cattacgtct    1620
aacgatattt acatgcttgg ttatgtttct aattctttaa ctggcccata caagccgctg    1680
aacaaaactg gccttgtgtt aaaaatggat cttgatccta acgatgtaac ctttacttac    1740
tcacacttcg ctgtacctca agcgaaagga acaatgtcg tgattacaag ctatatgaca    1800
aacagaggat tctacgcaga caaacaatca acgtttgcgc ctagcttcct gctgaacatc    1860
aaaggcaaga aacatctgt tgtcaaagac agcatccttg aacaaggaca attaacagtt    1920
aacaaataaa acgcaaaag aaaatgccga tatccagcgg cgtgcacacc ttcccggctg    1980
tcctacagtc ctcaggactc tactccctca gcagcgtggt gaccgtgccc tccagcagct    2040
tgggcaccca gacctacacc tgcaacgtga atcacaagcc cagcaacacc aaggtggaca    2100
agagagttga gcccaaatct tgtgacaaaa ctcacacatg cccaccgtgc ccagcacctg    2160
aactcctggg gggaccgtca gtcttcctct tccccccaaa acccaaggac accctcatga    2220
tctcccggac ccctgaggtc acatgcgtgg tggtggacgt gagccacgaa gaccctgagg    2280
tcaagttcaa ctggtacgtg gacggcgtgg aggtgcataa tgccaagaca aagccgcggg    2340
aggagcagta caacagcacg taccgtgtgg tcagcgtcct caccgtcctg caccaggact    2400
ggctgaatgg caaggagtac aagtgcaagg tctccaacaa agccctccca gcccccatcg    2460
agaaaaccat ctccaaagcc aaagggcagc cccgagaacc acaggtgtac accctgcccc    2520
catcccggga tgagctgacc aagaaccagg tcagcctgac ctgcctggtc aaaggcttct    2580
atcccagcga catcgccgtg gagtgggaga gcaatgggca gccggagaac aactacaaga    2640
ccacgcctcc cgtgctggac tccgacggct ccttcttcct ctacagcaag ctcaccgtgg    2700
acaagagcag gtggcagcag gggaacgtct tctcatgctc cgtgatgcat gagggtctgc    2760
acaaccacta cacgcagaag agcctctccc tgtctccggg taaatgagtg cgacggcggc    2820
cgc                                                                 2823
```

<210> SEQ ID NO 19
<211> LENGTH: 35
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (35)..(35)
<223> OTHER INFORMATION: n is a, c, g, or t

<400> SEQUENCE: 19

```
cggtaccgcg ggcccgggat ccccccccccc cccdn                                 35
```

<210> SEQ ID NO 20
<211> LENGTH: 27
<212> TYPE: DNA
<213> ORGANISM: Artificial sequence
<220> FEATURE:
<223> OTHER INFORMATION: Primer

<400> SEQUENCE: 20

```
<210> SEQ ID NO 21
<211> LENGTH: 25
<212> TYPE: DNA
<213> ORGANISM: Artificial sequence
<220> FEATURE:
<223> OTHER INFORMATION: Primer

<400> SEQUENCE: 21
agccgggaag gtgtgcacgc cgctg                                                25

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
aggtgtgcac gccgctggtc                                                      20

<210> SEQ ID NO 23
<211> LENGTH: 23
<212> TYPE: DNA
<213> ORGANISM: Artificial sequence
<220> FEATURE:
<223> OTHER INFORMATION: Primer

<400> SEQUENCE: 23
cacgccgctg gtcagggcgc ctg                                                  23

<210> SEQ ID NO 24
<211> LENGTH: 23
<212> TYPE: DNA
<213> ORGANISM: Artificial sequence
<220> FEATURE:
<223> OTHER INFORMATION: Primer

<400> SEQUENCE: 24
ctggtcaggg cgcctgagtt cca                                                  23
```

The invention claimed is:

1. A method for homologous recombination comprising:
amplifying nucleic acid molecules in a sample, which sample includes a nucleic acid molecule comprising a target gene sequence, by polymerase chain reaction ("PCR") using an amplification primer containing P1 sequence and an amplification primer containing P2 sequence to obtain a PCR product having primer sequence P1 on one end of the PCR product and primer sequence P2 on the other end of the PCR product and which sample further includes a nucleic acid molecule comprising a non-target gene sequence;
providing a linearized vector, wherein
the linearized vector has homologous recombination regions on its terminal ends, one end comprising VP1 and VT1 and the other end comprising VP2, or VP2 and VT2, wherein
(i) VP1, comprising a nucleotide sequence homologous to the amplification primer sequence P1 and
(ii) VP2 comprising a nucleotide sequence homologous to the amplification primer sequence P2 and
(iii) a homologous recombination region VT1 comprising a nucleotide sequence homologous to a sequence T1, which T1 is a part of the target gene sequence in the PCR product internal to P1, wherein T1 comprises a sequence that is not part of P1, wherein VT1 is on the terminal side of VP1 and/or (iv) a homologous recombination region VT2 comprising a nucleotide sequence homologous to a sequence T2, which T2 is a part of sequence in the PCR product internal to P2 wherein T2 comprises a sequence that is not part of P2, wherein VT2 is on the terminal side of VP2, combining the PCR product, without purification, and the linearized vector under conditions suitable for homologous recombination, whereby the amplified nucleic acid molecule comprising the target gene sequence may be inserted into the linearized vector by homologous recombination (a) between the P1 and T1 sequences of the amplified nucleic acid molecule comprising the target gene sequence and the VP1 and T1 sequences on the linearized vector, and (b) between (i) the P2 sequence on the amplified nucleic acid molecule comprising the target gene sequence and the VP2 sequence on the linearized vector or (ii) the P2 and T2 sequences on the amplified nucleic acid molecule comprising the target gene sequence with the VP2 and VT2 sequences on the linearized vector; and obtaining a recombinant DNA molecule in which the amplified nucleic acid molecule comprising the target gene sequence is specifically inserted into the vector.

2. The method of claim 1, wherein both T1 and T2 have a nucleotide sequence specific to the target gene.

3. The method of claim 1, wherein at least one of the amplification primers P1 and P2 has a nucleotide sequence specific to the target gene.

4. The method of claim 1, wherein the PCR product is prepared by first and second PCR operations, the first PCR operation is conducted by using an amplification primer containing T1 sequence and an amplification primer containing P3 sequence, provided that the P3 sequence has no homology to any of homologous recombination regions of the vector VT1, VP1, VT2 and VP2, and the second PCR operation is conducted by using the amplification primer containing P1 sequence and the amplification primer containing P2 sequence, and wherein the amplification primer containing P1 sequence and the amplification primer containing P3 sequence have or do not have a partially overlapped sequence.

5. The method of claim 4, wherein the 3'-terminal side region of the amplification primer containing P1 sequence and the 5'-terminal side region of the amplification primer containing T1 sequence have a partially overlapped sequence, and the amplification primer containing P2 sequence and the amplification primer containing P3 sequence have or do not have a partially overlapped sequence.

6. The method of claim 1, wherein the amplification primer sequence P1 has 10 or more bases and the amplification primer sequence P2 has 10 or more bases.

7. The method of claim 1, wherein the homologous recombination regions of the vector VP1+VT1 has 11 or more bases and the homologous recombination region of the vector VP2+VT2 has 11 more bases.

8. The method of claim 1, wherein one or both of the amplification primers corresponding to sequences P1 and P2 are derived from nuclease resistant oligo primer.

9. The method of claim 1, wherein the target gene is an antibody gene or T-cell receptor gene, and contains a sequence derived from constant region and a sequence derived from variable region of the antibody gene or the T-cell receptor gene, and at least one of the homologous recombination regions of the vector VP1+VT1 and VP2+VT2 is a sequence derived from constant region of the antibody gene or the T-cell receptor gene.

10. The method of claim 9, wherein another of the homologous recombination regions of the vector VP1+VT1 and VP2+VT2 has a sequence which is not derived from the antibody gene or the T-cell receptor gene.

11. The method of claim 1, wherein the homologous recombination reaction is conducted in a cell by using Red (Red $\alpha/\beta$) or RecE/T system.

12. The method of claim 1, wherein the homologous recombination reaction is conducted in vitro and wherein the PCR product is incubated with vaccinia virus DNA polymerase to produce a 5' overhanging sequence of single-stranded DNA and then combined with the linearized vector.

13. A cloning method for a target gene comprising:

preparing a recombinant DNA molecule in which a nucleic acid molecule comprising the target gene sequence is specifically inserted into a vector by the method of any one of claims 1 to 12, and transforming a host cell with the recombinant DNA molecule and culturing the transformed host cell to amplify the recombinant DNA molecule.

* * * * *